US011376232B2

(12) United States Patent
Gröppel et al.

(10) Patent No.: US 11,376,232 B2
(45) Date of Patent: Jul. 5, 2022

(54) VIDOFLUDIMUS FOR USE IN THE TREATMENT OR PREVENTION OF VIRAL DISEASES

(71) Applicant: Immunic AG, Gräfelfing (DE)

(72) Inventors: Manfred Gröppel, Erlangen (DE); Daniel Vitt, Germering (DE); Hella Kohlhof, Munich (DE); Andreas Mühler, Munich (DE)

(73) Assignee: Immunic AG, Gräfelfing (DE)

( * ) Notice: Subject to any disclaimer, the term of this patent is extended or adjusted under 35 U.S.C. 154(b) by 0 days.

(21) Appl. No.: 17/234,986

(22) Filed: Apr. 20, 2021

(65) Prior Publication Data
US 2021/0322351 A1    Oct. 21, 2021

(30) Foreign Application Priority Data

Apr. 21, 2020 (EP) ...................... 20170729
Jul. 3, 2020 (EP) ...................... 20184031
Mar. 24, 2021 (EP) ...................... 21164552

(51) Int. Cl.
*A61K 31/196* (2006.01)
*A61P 31/14* (2006.01)
*A61K 9/00* (2006.01)
*A61K 9/20* (2006.01)
*A61K 31/706* (2006.01)
*A61K 45/06* (2006.01)

(52) U.S. Cl.
CPC .......... *A61K 31/196* (2013.01); *A61K 9/0053* (2013.01); *A61K 9/20* (2013.01); *A61K 31/706* (2013.01); *A61K 45/06* (2013.01); *A61P 31/14* (2018.01); *C07B 2200/13* (2013.01)

(58) Field of Classification Search
CPC .................................... A61K 31/196
See application file for complete search history.

(56) References Cited

U.S. PATENT DOCUMENTS

| | | | |
|---|---|---|---|
| 7,423,057 B2 | 9/2008 | Leban et al. | |
| 8,354,433 B2 * | 1/2013 | Vitt | C07D 333/38 514/332 |
| 8,653,138 B2 * | 2/2014 | Ammendola | A61P 17/02 514/563 |
| 9,795,590 B2 | 10/2017 | Strobl | |
| 10,874,687 B1 | 12/2020 | Sommadossi et al. | |
| 2020/0276219 A1 | 9/2020 | Painter et al. | |
| 2020/0360324 A1 | 11/2020 | Gröppel et al. | |
| 2021/0017125 A1 | 1/2021 | Vitt et al. | |

FOREIGN PATENT DOCUMENTS

| | | |
|---|---|---|
| WO | 03006424 A1 | 1/2003 |
| WO | 10128050 A2 | 11/2010 |
| WO | 12001148 A1 | 1/2012 |
| WO | 12001151 A1 | 1/2012 |
| WO | 15154820 A1 | 10/2015 |
| WO | 19101888 A1 | 5/2019 |
| WO | 19113462 A1 | 6/2019 |
| WO | 19175396 A1 | 9/2019 |
| WO | 21011572 A1 | 1/2021 |

OTHER PUBLICATIONS

Sleeman et al. Emerg Infect Dis, 2013, 19(9):1521-4 (abstract).*
Mavrodiev et al. "On Classification and Taxonomy of Coronaviruses (Riboviria, Nidovirales, Coronaviridae) with the special focus on severe acute respiratory syndromerelated coronavirus 2 (SARS-Cov-2)", bioRxiv preprint, published Oct. 19, 2020. DOI: 10.1101/2020.10.17.343749 (pp. 1-38).
Totura et al. "Broad-spectrum coronavirus antiviral drug discovery", Expert Opinion on Drug Discovery 2019, 14, 397, published online Mar. 8, 2019. DOI: 10.1080/17460441.2019.1581171.
Muehler A et al. "The Selective Oral Immunomodulator Vidofludimus in Patients with Active Rheumatoid Arthritis: Safety Results from the Component Study", Drugs in R&D 2019, 19(4), 351-366, published online Oct. 16, 2019. DOI: 10.1007/s40268-019-00286-z.
Muehler et al. "Safety, tolerability and pharmacokinetics of vidofludimus calcium (IMU-838) after single and multiple ascending oral doses in healthy male subjects", European Journal of Drug Metabolism and Pharmacokinetics 2020, 45, 557, published online May 2, 2020. DOI: 10.1007/s13318-020-00623-7.
Muehler et al. "Vidofludimus calcium, a next generation DHODH inhibitor for the treatment of relapsing-remitting multiple sclerosis" Multiple Sclerosis and Related Disorders 2020, 43, 102129, published online Apr. 12 DOI: 10.1016/i.msard.2020.102129 2020.

(Continued)

*Primary Examiner* — Rei Tsang Shiao
(74) *Attorney, Agent, or Firm* — Millen White Zelano & Branigan, PC; Brion P. Heaney

(57) ABSTRACT

The present invention relates to a compound according to Formula (I)

Formula (I)

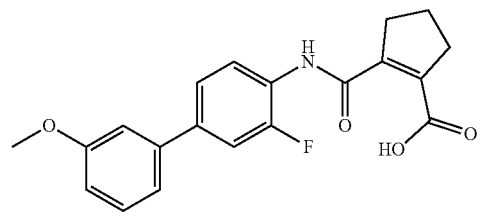

or a salt, solvate and/or a hydrate thereof, wherein said compound inhibits dihydroorotate dehydrogenase (DHODH), for use in the treatment and prevention of viral infection. A preferred example is viral infection caused by coronavirus, in particular betacoronavirus, more particular SARS-CoV-2 and mutated versions thereof.

29 Claims, No Drawings

(56) References Cited

OTHER PUBLICATIONS

Kim et al. "Novel dihydroorotate dehydrogenase inhibitors with potent interferon-independent antiviral activity against mammarenaviruses in vitro", Viruses 2020, 12, 821, published online Jul. 29, 2020. DOI: 10.3390/v12080821.
Hahn et al. "IMU-838, a developmental DHODH inhibitor in phase II for autoimmune disease, shows anti-SARS-CoV-2 and broad-spectrum antiviral efficacy in vitro", Viruses 2020, 12, 1394, published online Dec. 5, 2020. DOI: 10.3390/v12121394.
De Julian-Ortiz et al. "Virtual combinatorial syntheses and computational screening of new anti-herpes compounds", Journal of Medicinal Chemistry 1999, 42, 3308, published Aug. 3, 1999. DOI: 10.1021/jm981132u.
Xiong et al. "Novel and potent inhibitors targeting DHODH, a rate-limiting enzyme in de novo pyrimidine biosynthesis, are broad-spectrum antiviral against RNA viruses including newly emerged coronavirus SARS-CoV-2", Protein Cell 2020, 11, 723, published online Mar. 12, 2020. DOI: 10.1101/2020.03.11.983056.
Panoptes GmbH "Das Wiener Biotech Unternehmen Panoptes Pharma Gmbh ist in Besitz eines vielversprechenden Wirkstoffs gegen Covid-19" press release, posted online Mar. 25, 2020. (1 page).
Calistri et al. "The new generation hDHODH inhibitor MEDS433 hinders the in vitro replication of SARS-CoV", bioRxiv preprint, published online Dec. 7, 2020. DOI: 10.1101/2020.12.06.412759 (pp. 1-13).
Luban et al. "The DHODH inhibitor PTC299 arrests SARS-CoV-2 replication and suppresses induction of inflammatory cytokines", Virus Research 2021, 292, 198246, published online Nov. 26, 2020. DOI: 10.1016/j.virusres.2020.198246.
Hoffmann et al. "Broad-spectrum antiviral that interferes with de novo pyrimidine biosynthesis", Proceedings of the National Academy of Sciences of the United States of America 2011, 108, 5777, published Apr. 5, 2011. DOI: 10.1073/pnas.1101143108.
Wang et al. "Inhibition of Dengue virus through suppression of host pyrimidine biosynthesis", Journal of Virology 2011, 85, 6548, published online Apr. 20, 2011. DOI: 10.1128/JVI.02510-10.
Lucas-Hourani et al. "Inhibition of pyrimidine biosynthesis pathway suppresses viral growth through innate immunity", PLoS Pathogen 2013, 9, e1003678, published online Oct. 3, 2013. DOI: 10.1371/journal.ppat.1003678.
Doykov et al. "The long tail of Covid-19'—The detection of a prolonged inflammatory response after a SARS-CoV-2 infection in asymptomatic and mildly affected patients", F1000Research 2021, 9, 1349, published online Nov. 19, 2020. DOI: 10.12688/f1000research.27287.1.
Hanke T et al, "Small molecules with anti-inflammatory properties in clinical development", Pharmacology & Therapeutics, 2016, 157, 163-187, published online Nov. 26, 2015. DOI: 10.1016/j.pharmthera.2015.11.011.
Leban J et al, "SAR, species specificity, and cellular activity of cyclopentene dicarboxylic acid amides as DHODH inhibitors", Bioorg Med Chem Lett, 2005, 15(21), 4854-1857, published online Sep. 6, 2005. DOI: 10.1016/j.bmcl.2005.07.053.
Leban J et al, "Discovery of a novel series of DHODH inhibitors by a docking procedure and QSAR refinement", Bioorg Med Chem Lett. 2004, 14(1), 55-58, published online Dec. 2, 2003. DOI: 10.1016/j.bmcl.2003.10.021.
Baumgartner R et al, "Dual Binding Mode of a Novel Series of DHODH Inhibitors", J. Med. Chem. 2006, 49, 1239-1247, published online Jan. 26, 2006. DOI: 10 1021/jm0506975.
"Immunic, Inc. Announces 200 Patients Enrolled in Its Phase 2 Calvid-1 Trial of IMU-838 for the Treatment of Moderate Covid-19, Allowing for Main Phase 2 Efficacy Analysis to Proceed", press release, Immunic Inc, Nov. 2, 2020 (Author unknown) (pp. 1-3).
"Immunic, Inc. Announces Results From Interim Safety Analysis and Recruitment Update From Its Ongoing Phase 2 Calvid-1 Trial of IMU838 in Patients With Moderate Covid-19", press release, Immunic Inc, Sep. 28, 2020 (Author unknown) (pp. 1-4).
"Immunic Therapeutics Inaugural R&D Day", presentation from Immunic Virtual R&D Day, May 19, 2020 (Author unknown) (pp. 1-169).
"Developing Selective Oral DHODH Inhibitor IMU-838as Covid-19 Therapy", presentation from Apr. 22, 2020 (Author unknown) (pp. 1-19).
Marschall et al, "Assessment of drug candidates for broad-spectrum antiviral therapy targeting cellular pyrimidine biosynthesis", Antiviral Research, 2013, 100, 640-648, published online Oct. 20, 2013. DOI: 10.1016/j.antiviral.2013.10.003.
Gusarov et al. "COSMO-RS-Based Descriptors for the Machine Learning-Enabled Screening of Nucleotide Analogue Drugs against SARS-CoV-2", J. Phys. Chem. Lett. 2020, 11, 9408, published online Oct. 26, 2020. DOI: 10.1021/acs.jpclett.0c02836.
Cuthbertson et al. "The dihydroorotate dehydrogenase inhibitor brequinar is synergistic with ENT1/2 inhibitors", ACS Pharmacology & Translational Science 2020, 3, 1242, publication date Nov. 23, 2020. DOI: 10.1021/acsptsci.0c00124.
Mestres "The target landscape of N4-hydroxycytidine based on its chemical neighborhood", bioRxiv preprint, published May 5, 2020. DOI: 10 1101/2020.03.30.016485 (pp. 1-12).
Halford "An emerging antiviral takes aim at Covid-19", CERN news, published May 5, 2020 (pp. 1-5).
Hoffman et al. "The discovery of ketone-based covalent inhibitors of coronavirus 3CL proteases for the potential therapeutic treatment of Covid-19", Journal of Medicinal Chemistry 2020, 63, 12725, published online Oct. 15, 2020. DOI: 10.1021/acs.jmedchem.0c01063.
Stegman et al. "The folate antagonist methotrexate diminishes replication of the coronavirus SARS-CoV-2 and enhances the antiviral efficacy of remdesivir in cell culture models", bioRxiv preprint, published online Jul. 20, 2020. DOI: 10.1101/2020.07.18.210013 (pp. 1-36).
"Pfizer Initiates Phase 1 Study of Novel Oral Antiviral Therapeutic Agent Against SARS-CoV-2", press release, published online Mar. 23, 2021 (pp. 1-2).
Painter et al. "Human safety, tolerability, and pharmacokinetics of a novel broad-spectrum oral antiviral compound, molnupiravir, with activity against SARS-CoV-2", medRxiv preprint, published online Dec. 14, 2020. DOI: 10.1101/2020.12.10.20235747 (pp. 1-32).
Abdelnabi et al. "The combined treatment of Molnupiravir and Favipiravir results in a marked potentiation of antiviral efficacy in a SARS-CoV-2 hamster infection model", bioRxiv preprint, published online Mar. 10, 2012. DOI: 10.1101/2020.12.10.419242 (pp. 1-17).
Tzou et al. "Coronavirus antiviral research database (CoV-RDB)—an online database designed to facilitate comparisons between candidate anti-coronavirus compounds", Viruses 2020, 12, 1006, published online Sep. 9, 2020. DOI :10.3390/v12091006 (pp. 1-21).
Lanevski et al. "Identification and tracking of antiviral drug combinations", Viruses 2020, 12, 1178, published online Oct. 18, 2020. doi:10.3390/v12101178 (pp. 1-20).
Ahamad et al. "Primed for global coronavirus pandemic: Emerging research and clinical outcome", European Journal of Medicinal Chemistry 2021, 209, 112862, published online Sep. 19, 2020. DOI: 10.1016/j.ejmech.2020.112862.
Al-Horani et al. "Potential anti-SARS-CoV-2 therapeutics that target the post-entry stages of the viral life cycle", Viruses 2020, 12, 1092, published online Sep. 26, 2020. DOI:10.3390/v12101092 (pp. 1-42).
Boschi et al. "Dihydroorotate dehydrogenase inhibitors in anti-infective drug research", European Journal of Medicinal Chemistry 2019, 183, 111681, published online Sep. 12, 2019. DOI: 10.1016/j.ejmech.2019.111681 (pp. 1-21).
Coelho et al. "Dihydroorotate dehydrogenase inhibitors in SARS-CoV-2 infection", European Journal of Clinical Investigation 2020, 50, e13366, published online Jul. 23, 2020. DOI: 10.1111/eci.13366 (pp. 1-5).
"WHO R&D Blueprint novel Coronavirus Covid-19 Therapeutic Trial Synopsis", published Feb. 18, 2020. (pp. 1-12).
Cox et al. "Therapeutically administered ribonucleoside analogue MK-4482/EIDD-2801 blocks SARS-CoV-2 transmission in fer-

(56) References Cited

OTHER PUBLICATIONS rets", Nature Microbiology 2021, 6, 11, published online Dec. 3, 2020. DOI: 10.1038/s41564-020-00835-2.

Cusinato et al. "Repurposing drugs for the management of Covid-19", Expert Opinion on Therapeutic Patents, 2021, in print, published online Dec. 6, 2020. DOI: 10.1080/13543776.2021.1861248.

Kaddoura et al. "Covid-19 Therapeutic Options Under Investigation", Frontiers in Pharmacology 2020, 11, 1196, published online Aug. 6, 2020. DOI: 10.3389/fphar.2020.01196.

Padhi et al. "Rational Design of the Remdesivir Binding Site in the RNA-dependent RNA Polymerase of SARS-CoV-2 Implications for Potential Resistance", bioRxiv preprint, published online Jun. 29, 2020. DOI: 10.1101/2020.06.27.174896 (pp. 1-20).
Sheahan et al. "An orally bioavailable broad-spectrum antiviral inhibits 1 SARS-CoV-2 and multiple 2 endemic, epidemic and bat coronavirus", bioRxiv preprint, published online Mar. 20, 2020. DOI: 10.1101/2020.03.19.997890 (pp. 1-34).
Wang et al. "RNA-dependent RNA polymerase of SARS-CoV-2 as a therapeutic target", Journal of Medical Virolology 2021, 93, 300, published online Jul. 7, 2020. DOI: 10.1002/jmv.26264.
Toogood et al. "Myalgic encephalomyelitis/chronic fatigue syndrome (ME/CFS): Where will the drugs come from?", Pharmacological Research 2021, 165, 105465, published online Jan. 30, 2021. DOI: 10.1016/j.phrs.2021.105465.
Liu et al. "Enhancing the Antiviral Efficacy of RNA-Dependent RNA Polymerase Inhibition by Combination with Modulators of Pyrimidine Metabolism", Cell Chemical Biology 2020, 27, 668, published online Jun. 18, 2020. DOI: 10.1016/j.chembiol.2020.05.002.
Munier-Lehmann et al. "On Dihydroorotate Dehydrogenases and Their Inhibitors and Uses", Journal of Medicinal Chemistry 2013, 56, 3148, published online Mar. 1, 2013. DOI: 10.1021/jm301848w.
Totura et al. "Broad-spectrum coronavirus antiviral drug discovery", Expert Opinion on Drug Discovery 2019, 14, 397, published online Feb. 7, 2019. DOI: 10.1080/17460441.2019.1581171.

* cited by examiner

VIDOFLUDIMUS FOR USE IN THE TREATMENT OR PREVENTION OF VIRAL DISEASES

The present invention relates to a compound according to Formula (I) or a salt, solvate and/or a hydrate thereof, wherein said compound inhibits dihydroorotate dehydrogenase (DHODH), for use in the treatment and prevention of viral infection, preferably caused by coronavirus. The present invention particularly relates to viral infection caused by coronavirus, in particular by betacoronavirus and mutated versions thereof.

BACKGROUND OF THE INVENTION

Betacoronaviruses (β-CoVs or Beta-CoVs) are one of four genera of coronaviruses of the subfamily Orthocoronavirinae in the family Coronaviridae, of the order Nidovirales. They are enveloped, positive-sense, single-stranded RNA viruses of zoonotic origin.

Recently, a novel coronavirus emerged in the Chinese city of Wuhan in December 2019. After human coronavirus 229E (HCoV-229E) (classified in the genus *Alphacoronavirus*) and HCoV-OC43 (Betacoronavirus lineage 2a member) described in the 1960s, SARS-CoV-1 (Betacoronavirus lineage 2b member) that emerged in March 2003, HCoV-NL63 (*Alphacoronavirus* lineage 1b member) described in 2004, HCoV-HKU1 (Betacoronavirus lineage 2a member) discovered in 2005, and finally MERS-CoV that emerged in 2012 (classified in Betacoronavirus lineage 2c), the novel coronavirus is the seventh human coronavirus described to date as being responsible for respiratory infection. Evidence was rapidly reported that patients were suffering from an infection with a novel Betacoronavirus tentatively named 2019 novel coronavirus (2019-nCoV). Despite drastic containment measures, the spread of 2019-nCoV, now officially known as severe acute respiratory syndrome coronavirus 2 (SARS-CoV-2), is ongoing. Phylogenetic analysis of this virus indicated that it is different (~80% nucleotide identity) but related to SARS-CoV-1. The classification and taxonomy of coronaviruses with special focus on SARS-CoV-2 has been described by Mavrodiev et al. (doi.org/10.1101/2020.10.17.343749).

The World Health Organization (WHO) declared severe acute respiratory syndrome coronavirus 2 (SARS-CoV-2) infections (causing coronavirus disease 2019, COVID-19) a pandemic on Mar. 11, 2020. Main clinical symptoms include fever, cough, myalgia or fatigue, expectoration, and dyspnea. While a majority of patients do not experience severe symptoms, one meta-analysis found that approximately 18% of cases were severe. Fatality rates are estimated to be approximately 0.5 to 10% at this time.

It appears that there are two distinct but overlapping pathological subsets of COVID-19, the first triggered by the virus itself and the second, the host response. The initial stage occurs at the time of inoculation and early establishment of disease. For most people, this involves an incubation period associated with mild and often non-specific symptoms such as malaise, fever and a dry cough. At this stage it is reported that the virus replicates in the upper respiratory tract. Treatment at this stage is primarily targeted towards symptomatic relief. In the second stage of established pulmonary disease, viral multiplication and localized inflammation in the lung is the norm. During this stage, patients develop a viral pneumonia, with cough, fever and possibly hypoxia. Treatment would primarily consist of supportive measures and available antiviral therapies. If hypoxia ensues (Stage IIb), it is likely that patients will progress to requiring mechanical ventilation and, in this situation, the use of anti-inflammatory therapy may be useful. A minority of COVID-19 patients will transition into the third and most severe stage of illness, which manifests as an extra-pulmonary systemic hyperinflammation syndrome. In this stage, markers of systemic inflammation appear to be elevated, including cytokines and interleukins. In this stage, shock, vasoplegia, respiratory failure and even cardiopulmonary collapse are discernable. Systemic organ involvement, even myocarditis, would manifest during this stage. Tailored therapy in stage III hinges on the use of immunomodulatory agents to reduce systemic inflammation before it overwhelmingly results in multi-organ dysfunction.

As of March 2020, no vaccine is available and, although numerous pharmacological interventions are under clinical investigation, clear efficacy has not yet been determined for any drug. Based on lessons learned from MERS and SARS outbreaks, lack of drugs capable of pan-coronavirus antiviral activity increases the vulnerability of public health systems to a highly pathogenic coronavirus pandemic (*Expert Opin. Drug. Discov.* 2019; 14:397).

A medicament against rheumatoid arthritis with a new mechanism of action, leflunomide, was put on the market by the company Aventis under the tradename ARAVA [EP 780128, WO 97/34600]. Leflunomide has immunomodulatory as well as anti-inflammatory properties [EP 217206, DE 2524929]. The mechanism of action is based upon the inhibition of dihydroorotate dehydrogenase (DHODH), an enzyme of the pyrimidine biosynthesis. Another drug which is targeting DHODH is teriflunomide (AUBAGIO®), which is the metabolite of leflunomide. Teriflunomide is approved for the treatment of multiple sclerosis in some countries.

Vidofludimus (Formula I) (2-((3-fluoro-3'-methoxy-[1,1'-biphenyl]-4-yl)carbamoyl)cyclopent-1-enecarboxylic acid) is an orally available DHODH inhibitors with no structural similarity to other known drugs, including leflunomide and teriflunomide. Vidofludimus, in both its free acid form and its calcium salt formulation (vidofludimus calcium), has undergone clinical trials for a variety of immune-related indications. Both formulations depend on the same active substance (vidofludimus) in vivo, and thus the two formulations share the same mechanism of action, pharmacology, and toxicology. The safety of both vidofludimus and vidofludimus calcium has been investigated in healthy volunteers and patients with different immune-mediated diseases.

Formula (I)

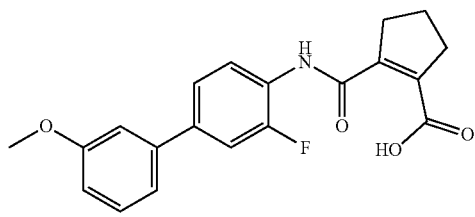

WO 2003/006424 and WO 2003/006425 describe certain specific compounds, which are reported to be useful for treatment and prevention of diseases where there is an advantage in inhibiting DHODH. WO 2010/128050 describes the use of these compounds as broad antiviral agents, in particular human cytomegalovirus (hCMV), human immunodeficiency virus (HIV), hepatitis C virus (HCV), hepatitis B virus (HBV) and influenza, while WO 2015/154820 describes the use of similar compounds as antiviral agents, in particular adeno virus, human herpesvirus (HHV), varicella zoster virus (VZV), herpes simplex virus (HSV), vaccinia virus or BK virus. Coronaviruses were not mentioned in this two applications. WO 2012/001148 describes calcium salts of the compound of Formula (I) which inhibit DHODH, and the preparation thereof (example 4). WO 2012/001151 describes other salts of the compound according Formula (I). WO 2019/175396 describes a new white crystalline calcium salt of vidofludimus and its solvates and hydrates (designated as "Polymorph A"), a process for its preparation, a composition comprising it and its use for the treatment of chronic inflammatory and/or autoimmune diseases. WO 2019/101888 discloses dosage regimen of vidofludimus (or salts thereof) for use in the prevention or treatment of chronic inflammatory and/or autoimmune diseases.

Muehler et al. (*Drugs R D* 2019; 19:351) report the safety data of vidofludimus from a phase II trial in patients with rheumatoid arthritis (the COMPONENT trial), a randomized, double-blind, placebo-controlled study to evaluate the efficacy, safety, and pharmacokinetics of vidofludimus 35 mg compared with placebo on methotrexate background therapy in subjects with RA. After the priority date the following data was published: Muehler et al. (*Eur. J. Drug Metab. Pharmacokinet.* 2020; 45:557) describes the safety, tolerability and pharmacokinetics of vidofludimus calcium in healthy male subjects. Muehler et al. (*Mult. Scler. Relat. Disord.* 2020; 43:102129) describes the use of vidofludimus calcium for the treatment of relapsing-remitting multiple sclerosis.

After filing, additional data emerged: Kim et al. (Viruses 2020; 12:821) describes the antiviral activity of vidofludimus against mammarena viruses. Hahn et al. (*Viruses* 2020; 12:1394) describes the anti-SARS-CoV-2 and broad-spectrum antiviral efficacy of vidofludimus.

De Julian-Ortiz et al. (*J. Med. Chem.* 1999; 42:3308) describes certain potential anti-herpes compounds with cyclopentenoic acid moieties.

Xiong et al. (*Protein Cell* 2020; 11:723) first described the inhibition of DHODH to treat RNA viruses including SARS-CoV-2 and also other groups mentioned similar results, e.g. Panoptes GmbH (press release) for PP-001. However vidofludimus was not mentioned as DHODH inhibitor. After the priority date additional data for DHODH inhibitors emerged, e.g. Calistri et al. (doi.org/10.1101/2020.12.06.412759) for MEDS433 or Luban et al. (*Virus Res.* 2021; 292:198246) for PTC299.

DETAILED DESCRIPTION

It is an object of the present invention to provide effective agents that can be used for the prevention and treatment of viral infection that can be treated/prevented by the inhibition of DHODH, in particular coronavirus infection. Other objects and advantages will become apparent to the person of skill when studying the present description of the present invention.

While most efforts to combat coronavirus infections are focused on drugs and vaccines aimed at viral targets, it is particularly important to explore additional treatment options targeting host cell factors that are able to act with less dependence on the genetic drift of viruses (i.e. mutations) and synergistically to standard-of-care antiviral therapies. With that in mind, DHODH inhibitors such as presented here, present a very promising approach by attacking the disease by three complementary mechanisms: a) inhibition of virus replication by depletion of nucleotide pool; b) induction of innate immune response by DHODH inhibition independent of interferon signaling; and c) inhibition of "overreacting", cytokine-high producing immune cells.

In the human body, DHODH catalyzes the synthesis of pyrimidines, which are in particular necessary for cellular metabolism. An inhibition of DHODH leads to block of transcription of sensitive genes in metabolically activated cells, whereas cells with normal metabolic activity obtain their required pyrimidine building blocks from the pyrimidine salvage pathway and show normal transcriptional activity. Disease relevant metabolically activated lymphocytes rely on de novo pyrimidine syntheses and react particularly sensitively to DHODH inhibition. Some substances that inhibit DHODH are important medicaments for the treatment of chronic inflammatory and auto-immune diseases.

In a first aspect of the present invention, this object is solved by a compound according to Formula (I) (vidofludimus, IMU-838)

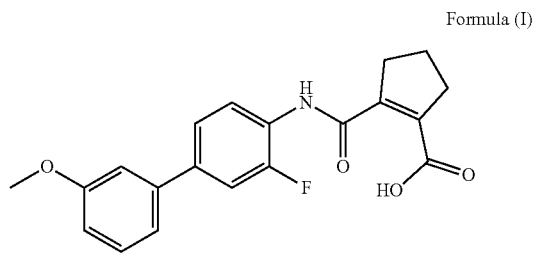 [SMILES: COc1cccc(-c2ccc(NC(=O)C3=C(C(=O)O)CCC3)c(F)c2)c1]

Formula (I)

a pharmaceutically acceptable salt, a solvate, a solvate of a salt, a hydrate or a polymorph thereof for use in the prevention and/or treatment of diseases caused by viral infection in a mammalian subject, such as a human.

One special embodiment is a compound according to Formula (I),

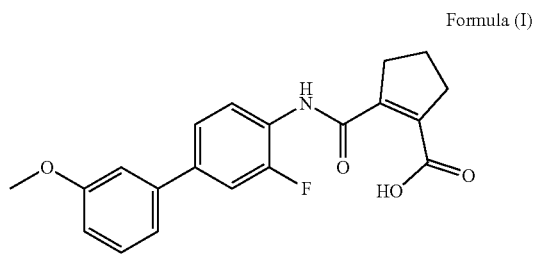 [SMILES: COc1cccc(-c2ccc(NC(=O)C3=C(C(=O)O)CCC3)c(F)c2)c1]

Formula (I)

a pharmaceutically acceptable salt, a solvate, a solvate of a salt, a hydrate or a polymorph thereof for use in the prevention and/or treatment of diseases caused by viral infection with coronaviruses in a mammalian subject, such as a human.

Pharmaceutically acceptable salt are known to a person skilled in the art and e.g. listed in P. H. Stahl and C. G. Wermuth (editors), *Handbook of Pharmaceutical Salts: Properties, Selection and Use*, Weinheim/Zürich:Wiley-VCH/VHCA, 2002. In the context of this invention is a pharmaceutically acceptable salt a physiologically acceptable salt.

It was surprisingly found that the compound according to Formula (I) (vidofludimus, IMU-838), as a DHODH inhibitor, was effective and exhibits many advantages compared to other antiviral treatment options. It targets the host cells— which provides broad-spectrum antiviral activity—blocks viral replication and overcomes potential viral mutagenesis. Additionally, it may act directly on the virus replication in the infected cells. Targeting virulence factors, such as cytokines, specifically benefits late and more severe cases. DHODH inhibition is only selective towards highly activated immune cells and infected cells and therefore does not cause broad and difficult to manage side effects seen with antimetabolites and nucleoside analogues. In contrast to approved DHODH inhibitors leflunomide and teriflunomide, the compound according to Formula (I) does not hit other off-targets like EGFR or Auroroa-A kinases. Therefore, also based on an excellent pharmacokinetic profile, a very good safety profile, vidofludimus represents a convenient, oral treatment option for viral infection, in particular of betacoronaviruses, specifically moderate-to-severe SARS-CoV-2 cases. In particular, vidofludimus has shown a very good blood plasma half-life of 30 hours in humans which allows a quick achievement of effective concentrations of the drug in patients, such as humans. In contrast, the blood plasma half-life of leflunomide is 16 to 19 days and its dosing to achieve therapeutic trough levels may take up to 2 months, unfeasibly for an acute disease in a virus infection.

In the context of the present invention, the term "vidofludimus" shall include the compound according to Formula (I) in its free acid form, and its pharmaceutically acceptable salt forms, such as the calcium, potassium, magnesium, choline or sodium salt. The term shall also include pharmaceutically acceptable solvates, hydrates, solvates of a salt, crystals and polymorphs. Preferred is vidofludimus calcium or vidofludimus choline.

"IMU-838" (also termed "vidofludimus calcium") is the calcium salt of vidofludimus, including pharmaceutically acceptable solvates, hydrates, crystals and polymorphs.

A preferred structure for IMU-838 is the dihydrate of 1-cyclopentene-1-carboxylic acid, 2-(((3-fluoro-3'-methoxy (1,1'-biphenyl)-4-yl)amino)carbonyl)-, calcium salt (2:1) with the structure as follows:

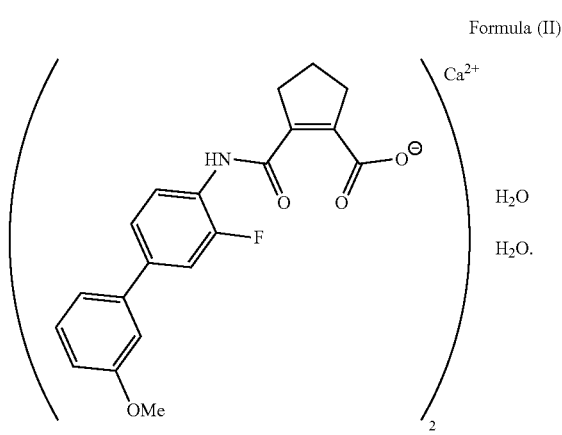

Formula (II)

The "Polymorph A" of IMU-838 is a white crystalline material of Formula (II) which is characterized as described in WO 2019/175396. In a special embodiment, "Polymorph A" of IMU-838 is characterized by an X-ray powder diffraction pattern having characteristic peaks at 2 theta (±0.2°) of 5.91°, 9.64°, 16.78°, 17.81°, 19.81° and 25.41°. In a particular special embodiment, "Polymorph A" of IMU-838 is characterized as outlined in FIG. 1 from WO 2019/175396.

Preferred is the compound for use according to the present invention, wherein said viral infection is by an RNA virus. RNA viruses can be single-stranded or double-stranded, and preferably include viruses that cause diseases in mammals, such as the human. Preferable examples are HIV, HCV, Ebola, rotavirus, Zika virus, polio virus, rhinovirus, hepatitis A virus, measles virus, mumps virus, RSV, rabies, Lassa virus, hantavirus, or influenza, in particular a single stranded RNA virus, such as HCoV-229E, HCoV-NL63, or betacoronaviruses, such as HCoV-OC43, SARS-CoV-1, HCoV-HKU1, MERS-CoV or SARS-CoV-2, which is particularly preferred.

One special embodiment is the compound for use according to the present invention, wherein said viral infection is caused by an RNA virus. RNA viruses can be single-stranded or double-stranded, and preferably include viruses that cause diseases in mammals, such as the human. Preferable examples are single stranded RNA virus, such as HCoV-229E, HCoV-NL63, or betacoronaviruses, such as HCoV-OC43, SARS-CoV-1, HCoV-HKU1, MERS-CoV or SARS-CoV-2, which is particularly preferred.

One particular special embodiment is the compound for use according to the present invention, wherein said viral infection is caused by betacoronaviruses, such as HCoV-OC43, SARS-CoV-1, HCoV-HKU1, MERS-CoV or SARS-CoV-2.

An even more special embodiment is the compound for use according to the present invention, wherein said viral infection is caused by SARS-CoV-2 or a mutated form of SARS-CoV-2.

An special embodiment is the compound for use according to the present invention, wherein said viral infection is caused by a mutated form of SARS-CoV-2.

An more special embodiment is the compound for use according to the present invention, wherein said viral infection is caused by a mutated form of SARS-CoV-2, wherein the strain is selected from B.1.1.7, B.1.351, P.1 and B.1.617.

An most special embodiment is the compound for use according to the present invention, wherein said viral infection is caused by SARS-CoV-2.

Antiviral effects by DHODH inhibition have been described for several RNA and DNA viruses, such as Ebola, HIV, HCV, hCMV and influenza. It has even been shown that, while other antiviral drugs are able to inhibit viral infection up to 4 hours after infection, DHODH inhibitors are still effective up to 12-16 hours after infection in in vitro assays (Hoffmann et al., *Proc. Natl. Acad. Sci.* 2011; 108: 5777; Wang et al., *J. Virol.* 2011; 85:6548). A direct as well as an indirect antiviral effect has been reported for DHODH inhibitors. These effects are both linked to blocking pyrimidine de novo synthesis. In the direct pathway, the reduction of pyrimidine neosynthesis is interfering with the viral transcription and replication.

However, Lucas-Hourani et al. (*PLoS Pathog.* 2013; 9:e1003678) reported that the main antiviral effect might rather be an indirect effect via the induction or amplification of interferon-stimulated genes due to the reduced pyrimidine synthesis. A large fraction of these genes play a role in the host innate immune defense to viruses. Interestingly, while these genes are normally induced by interferons, the upregulation of these genes by DHODH inhibitors is independent of interferons.

Xiong et al. (*Protein Cell* 2020; 11:723) proposes that DHODH inhibitors exert a strong activity against SARS-CoV-2 virus in in vitro cellular studies. DHODH inhibitors that were tested were leflunomide/teriflunomide and brequinar. However, due to unfavorable pharmacokinetic profiles (leflunomide/teriflunomide) and toxicity (brequinar), these drugs were regarded as not suitable as acute antiviral treatments. Interestingly, later-stage survival was 50% when treated with the DHODH inhibitor alone and 100% when treated with combination therapy (DHODH inhibitor+oseltamivir) in Influenza A infected (WSN or 2009 pandemic H1N1 virus) mice.

According to the present invention, a mammalian subject can be preferably selected from a mouse, rat, cat, dog, rabbit, goat, sheep, horse, camel, lama, cow, monkey, a farm animal, a sport animal, and a pet, and a human. In a special embodiment the species is human.

The subject is either infected with the virus, has been exposed to the virus or is at risk of being exposed to the virus.

According to the present invention, the compound is for use in viral infection, and therefore treats and/or prevents the related diseases or syndromes, such as, for example, AIDS, hepatitis, ebola, polio, diarrhea, measles, mumps, rabies, Lassa fever, viral flu, respiratory disease, acute respiratory disease, sepsis, acute respiratory distress syndrome, and adverse immune reactions, in particular moderate to severe cases of said diseases, and wherein said disease preferably is selected from diseases causes by SARS-CoV-2, in particular COVID-19, such as acute respiratory disease, sepsis, acute respiratory distress syndrome, and adverse immune reactions, such as a cytokine storm.

The compound for use according to the present invention, wherein said disease is selected from respiratory disease, acute respiratory disease, sepsis, acute respiratory distress syndrome, and adverse immune reactions (e.g. a cytokine storm), in particular moderate to severe cases of said diseases, and wherein said disease preferably is selected from diseases causes by SARS-CoV-2, in particular COVID-19, such as acute respiratory disease, sepsis, acute respiratory distress syndrome, and adverse immune reactions, such as a cytokine storm.

By "treatment" or "treating" is meant any treatment of a disease or disorder, in a mammal, including: preventing or protecting against the disease or disorder, that is, causing, the clinical symptoms of the disease not to develop; inhibiting the disease, that is, arresting or suppressing the development of clinical symptoms; and/or relieving the disease, that is, causing the regression of clinical symptoms. By "amelioration" is meant the prevention, reduction or palliation of a state, or improvement of the state of a subject; the amelioration of a stress is the counteracting of the negative aspects of a stress. Amelioration includes, but does not require complete recovery or complete prevention of a stress.

The term "organic acid derivative" means that the carboxylic acid moiety can be present as free acid or as a "prodrug" which themself can be biologically active or inactive, but are converted (for example metabolically or hydrolytically) into compounds according to the invention during their residence time in the body. An example of a prodrug is the ethyl ester of the carboxylic acid.

The term "pharmaceutically acceptable salts" (also termed "physiologically acceptable salt") refers to salts prepared from pharmaceutically acceptable bases, including inorganic bases and organic bases. The present disclosure provides the use of pharmaceutically acceptable salts of any compound described herein. Thus, the compounds of the present disclosure which contain acidic groups can be present on these groups and can be used according to the disclosure, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. Metal salts can arise from the addition of an inorganic base to a compound of the disclosure. The inorganic base consists of a metal cation paired with a basic counterion, such as, for example, hydroxide, carbonate, bicarbonate or phosphate. The metal can be an alkali metal, alkaline earth metal, transition metal or main group metal. In some embodiments, the metal is lithium, sodium, potassium, cesium, cerium, magnesium, manganese, iron, calcium, strontium, cobalt, titanium, aluminum, copper or zinc.

In some cases, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt or a zinc salt.

Ammonium salts can arise from the addition of ammonia or an organic amine to a compound of the disclosure. In some embodiments, the organic amine is triethylamine, diisopropylamine, ethanolamine, diethanolamine, triethanolamine, morpholine, N-methylmorpholine, piperidine, N-methylpiperidine, N-ethylpiperidine, dibenzylamine, piperazine, pyridine, pyrazole, imidazole or pyrazine.

In some cases, an ammonium salt is a triethylamine salt, a diisopropylamine salt, an ethanolamine salt, a diethanolamine salt, a triethanolamine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, an imidazole salt or a pyrazine salt.

The respective salts can be obtained by customary methods which are known to the person skilled in the art like, for example, by contacting these with an organic or inorganic base in a solvent or dispersant, or by cation exchange with other salts. The present disclosure also includes all salts of the compounds of the present disclosure which, owing to low physiological compatibility, are not directly suitable for use in pharmaceuticals but which can be used, for example, as intermediates for chemical reactions or for the preparation of pharmaceutically acceptable salts.

Further the compounds of the present disclosure may be present in the form of solvates, such as those which include as solvate water, or pharmaceutically acceptable solvates, such as alcohols, in particular ethanol. A stoichiometric or non-stoichiometric amount of solvent is bound by non-covalent intermolecular forces. When the solvent is water, the "solvate" is a "hydrate."

The term "polymorph" as used herein refers to a crystalline form of a compound or a salt, hydrate, or solvate thereof, in a particular crystal packing arrangement. All polymorphs have the same elemental composition. The term "crystalline," as used herein, refers to a solid state form which consists of orderly arrangement of structural units. Different crystalline forms of the same compound, or a salt, hydrate, or solvate thereof, arise from different packing of the molecules in the solid state, which results in different crystal symmetries and/or unit cell parameter. Different crystalline forms usually have different X-ray diffraction patterns, infrared spectra, melting points, density, hardness, crystal shape, optical and electrical properties, stability and solubility.

The term "effective amount" is meant to include the amount of a compound that, when administered, is sufficient to prevent development of, or alleviate to some extent, one or more of the symptoms of a disorder, disease, or condition being treated. The term "effective amount" also refers to the amount of a compound that is sufficient to elicit the biological or medical response of a cell, tissue, system, animal, or human, which is being sought by a researcher, veterinarian, medical doctor or clinician.

In another important aspect according to the present invention regarding the compound for use, said prevention and/or treatment is in combination with additional therapeutic agents such as other DHODH inhibitors (e.g. as described herein), and/or standard antiviral therapy (SAT), for example selected from at least one of neuraminidase inhibitors (e.g., oseltamivir, zanamivir), favipiravir, remdesivir, ribavirin (tribavirin), interferon alfa-2b/ribavirin systemic, interferon alpha 2a or 2b, inclusive any pegylated versions, chloroquine or hydroxychloroquine (given in combination with azithromycin), dolutegravir+rilpivirine (JULUCA®), dolutegravir+lamivudine (DOVATO®), ritonavir+lopinavir (KALETRA®), bictegravir+tenofovir alafenamide+emtricitabine (BIKTARVY®), dolutegravir+abacavir+lamivudine (TRIUMEQ®), elvitegravir+cobicistat+emtricitabine+tenofovir alafenamide (GENVOYA®), and elvitegravir+cobicistat+emtricitabine+tenofovir disoproxil fumarate+emtricitabine (STRIBILD®). Preferred is a combination with remdesivir, chloroquine or hydroxychloroquine.

A preferred combination for use according to the present invention is DHODH inhibitors (e.g. as described herein) with at least remdesivir, chloroquine or hydroxychloroquine, more preferably IMU-838+remdesivir, chloroquine or hydroxychloroquine.

In a special embodiment, the combination is the "Polymorph A" of IMU-838 together with remdesivir.

In some embodiments, a DHODH inhibitor of the disclosure is administered in combination with a prodrug of a nucleoside triphosphate inhibitor, such as an inhibitor of viral RNA-dependent RNA-polymerase (RdRp). In some embodiments, the prodrug is remdesivir. Remdesivir is a 1'-cyano-substituted adenine C-nucleoside ribose analogue prodrug that exhibits antiviral activity against multiple viral diseases, including Junin virus, SARS-CoV, SARS-CoV-2, MERS-CoV, Marburg virus, Ebola virus, Nipah virus, and Lassa fever virus. Upon administration of remdesivir and entry into a cell, remdesivir can be converted to the corresponding carboxylate by esterases such as carboxyesterase 1 (CES1) and cathepsin A (CTSA). The resulting carboxylate can undergo further breakdown to the monophosphate, which can then be processed by intracellular anabolism to the active nucleoside triphosphate (NTP), GS-443902. GS-443902 can then be incorporated into viral RNA-dependent RNA-polymerase, resulting in premature termination of viral RNA chains. Other examples that can be used in the subject compositions and methods include the parent nucleoside of remdesivir, (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (GS-441524).

In another important aspect according to the present invention regarding the compound for use, said prevention and/or treatment is in combination with other DHODH inhibitors (e.g. as described herein), and/or standard antiviral therapy (SAT).

Preferred is the combination with other DHODH inhibitors (e.g. as described herein), and/or standard antiviral therapy (SAT), for use according to the present invention, wherein said viral infection is caused by an RNA virus. RNA viruses can be single-stranded or double-stranded, and preferably include viruses that cause diseases in mammals, such as the human. Preferable examples are HIV, HCV, Ebola, rotavirus, Zika virus, polio virus, rhinovirus, hepatitis A virus, measles virus, mumps virus, RSV, rabies, Lassa virus, hantavirus, or influenza, in particular a single stranded RNA virus, such as HCoV-229E, HCoV-NL63, or betacoronaviruses, such as HCoV-OC43, SARS-CoV-1, HCoV-HKU1, MERS-CoV or SARS-CoV-2, which is particularly preferred.

A preferred combination for use according to the present invention is DHODH inhibitors (e.g. as described herein) with at least remdesivir, chloroquine or hydroxychloroquine, more preferably IMU-838+at least remdesivir, chloroquine or hydroxychloroquine for betacoronaviruses infection, in particular SARS-CoV-2.

One embodiment regarding the compound for use, said prevention and/or treatment is in combination with standard antiviral therapy (SAT), which comprises at least remdesivir.

One embodiment for use according to the present invention is the combination of IMU-838 together with oseltamivir for the treatment of betacoronavirus infections, in particular SARS-CoV-2. In a special embodiment, the combination is the "Polymorph A" of IMU-838 together with oseltamivir.

In another aspect of the present invention, in the combination with standard antiviral therapy (SAT), for use according to the present invention, the ratio of an effective amount of DHODH inhibitors to an effective amount of standard antiviral therapy (SAT), also referred herein as DHODH inhibitors/SAT, is from 0.1 to 10, from 0.2 to 10, from 0.2 to 1 or from 1 to 10.

In another aspect of the present invention, in the combination with standard antiviral therapy (SAT), for use according to the present invention, the ratio of an effective amount of DHODH inhibitors to an effective amount of standard antiviral therapy (SAT), also referred herein as DHODH inhibitors/SAT, is from 0.1 to 10, more preferably from 0.2 to 10, more preferably from 0.2 to 1 or from 1 to 10. A more preferred ratio for the combination of IMU-838+at least remdesivir is 10 or 0.2.

In another aspect of the present invention, the compound for use can be provided and/or is administered as a suitable pharmaceutical composition, such as a tablet, capsule, granule, powder, sachet, reconstitutable powder, dry powder inhaler and/or chewable. Such solid formulations may comprise excipients and other ingredients in suitable amounts. Such solid formulations may contain e.g. cellulose, cellulose microcrystalline, polyvidone, in particular FB polyvidone, magnesium stearate and the like. Administration, however, can also be carried out rectally, e.g. in the form of suppositories, or parenterally, e.g. in the form of injections or infusions, or percutaneously, e.g. in the form of ointments, creams or tinctures.

It is to be understood that the present compound and/or a pharmaceutical composition comprising the present compound is for use to be administered to a human patient. The term "administering" means administration of a sole therapeutic agent or in combination with another therapeutic agent. It is thus envisaged that the pharmaceutical composition of the present invention are employed in co-therapy approaches, i.e. in co-administration with other medicaments or drugs and/or any other therapeutic agent which might be beneficial in the context of the methods of the present invention. Nevertheless, the other medicaments or drugs and/or any other therapeutic agent can be administered separately from the compound for use, if required, as long as they act in combination (i.e. directly and/or indirectly, preferably synergistically) with the present compound for use.

Thus, the compounds for use of the invention can be used alone or in combination with other active compounds—for example with medicaments already known for the treatment of the aforementioned diseases, whereby in the latter case a favorable additive, amplifying or preferably synergistically effect is noticed.

Suitable amounts of a DODH inhibitor disclosed herein to be administered to humans can range from 5 to 500 mg, in particular 10 mg to 100 mg. For example, a therapeutically effective amount of DODH inhibitor described herein administered to a human can be from about 1 mg to about 5 mg, from about 5 mg to about 10 mg, from about 10 mg to about 15 mg, from about 15 mg to about 20 mg, from about 15 mg to about 25 mg, from about 15 mg to about 30 mg, from about 15 mg to about 35 mg, from about 15 mg to about 40 mg, from about 15 mg to about 45 mg, from about 15 mg to about 50 mg, from about 15 mg to about 55 mg, from about 15 mg to about 60 mg, from about 20 mg to about 25 mg, from about 20 mg to about 30 mg, from about 20 mg to about 35 mg, from about 20 mg to about 40 mg, from about 20 mg to about 45 mg, from about 20 mg to about 50 mg, from about 20 mg to about 55 mg, from about 20 mg to about 60 mg, from about 25 mg to about 30 mg, from about 30 mg to about 35 mg, from about 35 mg to about 40 mg, from about 40 mg to about 45 mg, from about 45 mg to about 50 mg, from about 50 mg to about 55 mg, from about 55 mg to about 60 mg, from about 60 mg to about 65 mg, from about 65 mg to about 70 mg, from about 70 mg to about 75 mg, from about 75 mg to about 80 mg, from about 80 mg to about 85 mg, from about 85 mg to about 90 mg, from about 90 mg to about 95 mg or from about 95 mg to about 100 mg. In some embodiments, the therapeutically effective amount is about 10 mg, about 15 mg, about 20 mg, about 25 mg, about 30 mg, about 35 mg, about 40 mg, about 45 mg, about 50 mg, about 55 mg or about 60 mg.

Pharmaceutical compositions as used may optionally comprise a pharmaceutically acceptable carrier. Pharmaceutically acceptable carriers or excipients include diluents (fillers, bulking agents, e.g. lactose, microcrystalline cellulose), disintegrants (e.g. sodium starch glycolate, croscarmellose sodium), binders (e.g. PVP, HPMC), lubricants (e.g. magnesium stearate), glidants (e.g. colloidal $SiO_2$), solvents/co-solvents (e.g. aqueous vehicle, propylene glycol, glycerol), buffering agents (e.g. citrate, gluconates, lactates), preservatives (e.g. Na benzoate, parabens (Me, Pr and Bu), BKC), anti-oxidants (e.g. BHT, BHA, Ascorbic acid), wetting agents (e.g. polysorbates, sorbitan esters), thickening agents (e.g. methylcellulose or hydroxyethylcellulose), sweetening agents (e.g. sorbitol, saccharin, aspartame, acesulfame), flavoring agents (e.g. peppermint, lemon oils, butterscotch, etc.), humectants (e.g. propylene, glycol, glycerol, sorbitol). Other suitable pharmaceutically acceptable excipients are inter alia described in Remington's Pharmaceutical Sciences, 15$^{th}$ Ed., Mack Publishing Co., New Jersey (1991) and Bauer et al., Pharmazeutische Technologie, 5th Ed., Govi-Verlag Frankfurt (1997). The person skilled in the art knows suitable formulations for vidofludimus and will readily be able to choose suitable pharmaceutically acceptable carriers or excipients, depending, e.g., on the formulation and administration route of the pharmaceutical composition.

The therapeutics can be administered orally, e.g. in the form of pills, tablets, coated tablets, sugar coated tablets, hard and soft gelatin capsules, solutions, syrups, emulsions or suspensions or as aerosol mixtures. Administration, however, can also be carried out rectally, e.g. in the form of suppositories, or parenterally, e.g. in the form of injections or infusions, or percutaneously, e.g. in the form of ointments, creams or tinctures. Specifically preferred is as vidofludimus choline as intravenous formulation, due to its improved solubility.

One embodiment according to the present invention is the oral or intravenous administration of IMU-838. One special embodiment according to the present invention is the oral or intravenous administration of "Polymorph A" of IMU-838. One particular embodiment according to the present invention is the oral administration of IMU-838. One particular special embodiment according to the present invention is the oral administration of "Polymorph A" of IMU-838.

In addition to the aforementioned compounds for use of the invention, the pharmaceutical composition can contain further customary, usually inert carrier materials or excipients. Such carriers can be used to formulate tablets, powders, pills, dragees, capsules, liquids, gels, syrups, elixirs, slurries, suspensions and the like, for oral ingestion by a subject. Thus, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants. They can also contain the aforementioned salts of two or more compounds for use of the invention and also other therapeutically active substances as described above.

A pharmaceutical composition can be administered in a local or systemic manner, for example, via injection of the compound directly into an organ, optionally in a depot or sustained release formulation. Pharmaceutical compositions can be provided in the form of a rapid release formulation, in the form of an extended release formulation or in the form of an intermediate release formulation. A rapid release form can provide an immediate release. An extended release formulation can provide a controlled release or a sustained delayed release.

For oral administration, pharmaceutical compositions can be formulated readily by combining the active compounds with pharmaceutically-acceptable carriers or excipients.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol or titanium dioxide, lacquer solutions and suitable organic solvents or solvent mixtures. Dyestuffs or pigments can be added to the tablets or dragee coatings, for example, for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine and plant gelatins. A gelatin can be alkaline-processed. The push fit capsules can contain the active ingredients in admixture with filler such as lactose, binders such as starches or lubricants such as talc or magnesium stearate and stabilizers. In soft capsules, the active compounds can be dissolved or suspended in suitable liquids, such as fatty oils, liquid paraffin or liquid polyethylene glycols. Stabilizers can be added. All formulations for oral administration are provided in dosages suitable for such administration.

For buccal or sublingual administration, the compositions can be tablets, lozenges or gels. Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing or dispersing agents. Pharmaceutical formulations for parenteral administration include aqueous solutions of the active compounds in water soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams and ointments. Such pharmaceutical compositions can contain solubilizers, stabilizers, tonicity enhancing agents, buffers and preservatives.

Formulations suitable for transdermal administration of the active compounds can employ transdermal delivery devices and transdermal delivery patches, and can be lipophilic emulsions or buffered aqueous solutions, dissolved or dispersed in a polymer or an adhesive. Such patches can be constructed for continuous, pulsatile or on demand delivery of pharmaceutical compounds. Transdermal delivery can be accomplished by means of iontophoretic patches. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically-acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin or the eye.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound described herein can be manufactured, for example, by mixing, dissolving, granulating, dragee-making, levigating, emulsifying, encapsulating, entrapping or compression processes.

The pharmaceutical compositions can include at least one pharmaceutically-acceptable carrier, diluent, or excipient and compounds described herein as free-acids or pharmaceutically-acceptable salt forms. The methods and pharmaceutical compositions described herein include the use of crystalline forms (e.g. "Polymorph A") and active metabolites of these compounds having the same type of activity.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams.

The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents and other pharmaceutically-acceptable additives.

Non-limiting examples of dosage forms suitable for use in the present disclosure include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals and any combination thereof.

Preferred is the compound for use according to the present invention, wherein said compound is administered to said subject in an effective dosage, for example of 45 mg daily, taken as 22.5 mg BID in the morning about 15-60 min before a meal, such as at least about 15 minutes, at least about 30 minutes, at least about 45 minutes or at least about 60 minutes before a meal, and in the evening at least 2 hours after any meal. Nevertheless, this exemplary dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal, in particular mammal including human, body weight particularly 1 to 50 mg/kg. Suitable dosage rates for larger mammals, for example humans, can be of the order of from about 10 mg to 3 g/day, conveniently administered once or in divided doses, e.g. 2 to 4 times a day, or in sustained release form. For example, a therapeutically effective amount of a DODH inhibitor of the disclosure can be administered over one dose per day, two doses per day, three doses per day, or four doses per day. In some embodiments, the therapeutically effective amount is about 5 mg two times per day, about 7.5 mg two times per day, about 10 mg two times per day, about 12.5 mg two times per day, about 15 mg two times per day, about 17.5 mg two times per day, about 20 mg two times per day, about 22.5 mg two times per day, about 25 mg two times per day, about 27.5 mg two times per day, or about 30 mg two times per day.

A compound (e.g. DODH inhibitor) can be administered as soon as is practical after the onset of a disease or condition is detected or suspected, and for a length of time necessary for the treatment of the disease, such as, for example, from about 1 week to about 3 weeks. In some embodiments, a compound disclosed herein is administered for the lifetime of a subject. In some embodiments, the length of time a DODH inhibitor of the disclosure can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks or about 20 weeks. The length of treatment can vary for each subject.

In general, a daily dose of approximately 10 mg to 100 mg, particularly 10 to 50 mg, per human individual is appropriate in the case of the oral administration. In the case of other administration forms too, the daily dose is found within similar ranges. It is desirable to reach a plasma level of the compound for use of between 0.1 to 50 µM.

In the context of the present invention, it was surprisingly found that the compound vidofludimus for use according to the present invention shows particular advantages both in the prevention of viral infection in particular with coronaviruses as well as in the treatment of later stages of the diseases, probably because DHODH inhibitors target a host cell factor, particularly as a combination treatment. Accordingly, the compounds described herein can be administered before, during or after the occurrence of a disease or condition, and the timing of administering the composition containing a compound can vary. For example, the compounds can be used as a prophylactic and can be administered continuously to subjects with a propensity to conditions or diseases to lessen or reduce a likelihood of the occurrence of the disease or condition. The compounds and compositions can be administered to a subject during or as soon as possible after the onset of the symptoms. The initial administration can be via any practical route, such as by any route described herein using any formulation described herein.

In the preventive approach, the compound for use according to the present invention can be administered to a subject immediately after detection of infection.

In the preventive approach, the compound for use according to the present invention can be administered to a subject "late" and is still effective, e.g. when administered at between 8 to 24 hours post infection, preferably at between 10 to 20 hours post infection, more preferably at 12 to 16 hours post infection. This regimen still provides a surprisingly low viral load.

Since it the case of a coronavirus infection it may be difficult to determine the exact timepoint of infection, the compound for use according to the present invention can be administered to a subject "late" and is still effective, e.g. when administered at between 8 to 24 hours after a positive test towards coronaviruses or first signs of symptoms.

In the treatment approach, the compound for use according to the present invention can be administered to a subject immediately post infection.

In the treatment approach, the compound for use according to the present invention can be administered to a subject "late" in the infection cycle, and is still effective, in particular as a (synergistic) combination therapy, e.g. when administered at between 5 to 14 days post infection, preferably at between 5 to 11 days post infection, more preferably at 7 to 11 days post infection. This regimen provides a surprisingly effective treatment effect, and furthermore helps to control excessive immune reactions, like cytokine storms.

The treatment approach is also suitable to treat "long COVID" symptoms, even weeks post infection. The most commonly reported "long COVID" symptoms include fatigue, dyspnea, cough, arthralgia and chest pain. Other reported symptoms include cognitive impairment, depression, myalgia, headache, fever and palpitations. Biomarkers for "long COVID" symptoms are described e.g. in Doykov et al. *F1000Research* 2021; 9:1349.

One embodiment according to the present invention is the oral administration of IMU-838 for the treatment of "long COVID" symptoms. One special embodiment according to the present invention is the oral administration of "Polymorph A" of IMU-838 for the treatment of "long COVID" symptoms.

Activation of innate immunity is mainly induced by interferons in virus infected cells, but viruses like SARS-CoV-2 are able to block interferons by virus produced interferon antagonists. In infected and DHODH treated cells, the induction of genes inducing an innate immunity response is independent of interferons, but dependent on interferon regulatory transcription factor (IRF1), potentially by Ataxia Telangiectasia Mutated (ATM) expression induced by cellular stress signal.

In another aspect of the compound for use according to the present invention the prevention and/or treatment further comprises monitoring in said subject of at least one biomarker selected from the group of mean viral load, qualitative virological clearance of nasopharyngeal or respiratory samples using RT PCR test, D-dimer, LDH, C-reactive protein (CRP), IL-17, IFN-γ, IL-1ß, IL-6, TNFa, seroconversion, and IgM and IgG neutralizing antibodies. This monitoring usually is performed on a biologically sample taken from the mammalian subject, and comprises commonly known tests, for example antibody based, PCR based, and the like. The tests are repeated over time, and can be compared to control samples and/or samples taken earlier from the mammalian subject. The results help the attending physician to maintain or modify the course of a treatment, usually based on the severity of the clinical symptoms of the viral disease as treated.

In another aspect of the compound for use according to the present invention the prevention and/or treatment of "long COVID" symptoms further comprises monitoring in said subject with suitable biomarkers e.g. peroxiredoxin 3 (PRDX3), carbamoyl phosphate synthase (CPS1), N-Myc downstream regulated gene 1 (NDRG1), collagen triple helix repeat containing 1 (CTHRC1), cystatin C (CYTC) or progranulin (GRN).

In another aspect thereof, the present invention provides methods for preventing and/or treating viral infection in a mammalian subject, such as a human, comprising administering to said mammal an effective amount of a compound according to Formula (I) (vidofludimus, IMU-838), Formula (I)

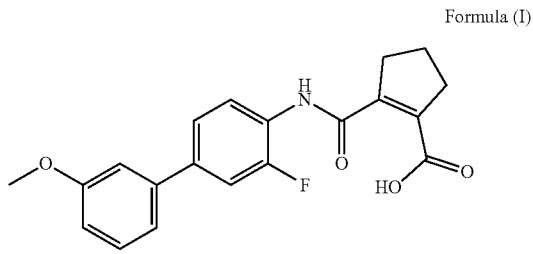

a pharmaceutically acceptable salt, a solvate, a solvate of a salt, a hydrate or a polymorph thereof. Preferred is vidofludimus calcium or choline.

In another aspect thereof, the present invention provides methods for preventing and/or treating viral infection caused by coronaviruses in a mammalian subject, such as a human, comprising administering to said mammal an effective amount of a compound according to Formula (I), Formula (I)

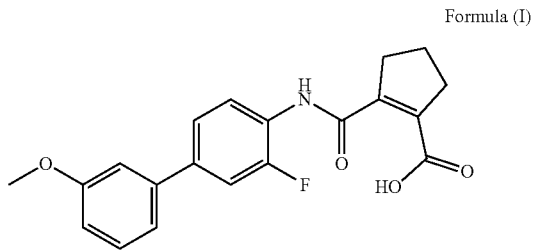 [SMILES: COc1cccc(-c2ccc(NC(=O)C3=C(C(=O)O)CCC3)c(F)c2)c1]

a pharmaceutically acceptable salt, a solvate, a solvate of a salt, a hydrate or a polymorph thereof.

The method comprises treating and/or ameliorating symptoms associated with viral infection in a mammalian subject, comprising administering to the subject vidofludimus (IMU-838) in a pharmaceutically effective amount, and by said administering, reducing symptoms associated with said viral infection, such as symptoms of AIDS, hepatitis, ebola, polio, diarrhea, measles, mumps, rabies, Lassa fever, viral flu, respiratory disease, acute respiratory disease, sepsis, acute respiratory distress syndrome, and adverse immune reactions, in particular moderate to severe cases of said diseases, and wherein said disease preferably is selected from diseases causes by SARS-CoV-2, in particular COVID-19, such as acute respiratory disease, sepsis, acute respiratory distress syndrome, and adverse immune reactions, such as a cytokine storm.

Preferred is the method according to the present invention, wherein said viral infection is caused by an RNA virus. RNA viruses can be single-stranded or double-stranded, and preferably include viruses that cause diseases in mammals, such as the human. Preferable examples are HIV, HCV, Ebola, rotavirus, Zika virus, polio virus, rhinovirus, hepatitis A virus, measles virus, mumps virus, RSV, rabies, Lassa virus, hantavirus, or influenza, in particular a single stranded RNA virus, such as HCoV-229E, HCoV-NL63, or betacoronaviruses, such as HCoV-OC43, SARS-CoV-1, HCoV-HKU1, MERS-CoV or SARS-CoV-2, which is particularly preferred.

One special embodiment is the method according to the present invention, wherein said viral infection is caused by an RNA virus. RNA viruses can be single-stranded or double-stranded, and preferably include viruses that cause diseases in mammals, such as the human. Preferable examples are single stranded RNA virus, such as HCoV-229E, HCoV-NL63, or betacoronaviruses, such as HCoV-OC43, SARS-CoV-1, HCoV-HKU1, MERS-CoV or SARS-CoV-2, which is particularly preferred.

One particular special embodiment is the method according to the present invention, wherein said viral infection is caused by betacoronaviruses, such as HCoV-OC43, SARS-CoV-1, HCoV-HKU1, MERS-CoV or SARS-CoV-2.

An even more special embodiment is the method according to the present invention, wherein said viral infection is caused by SARS-CoV-2 or a mutated form of SARS-CoV-2.

An most special embodiment is the method according to the present invention, wherein said viral infection is caused by SARS-CoV-2.

Combination or Alternation Therapy

The compounds or their pharmaceutically acceptable salts as described herein can be administered on top of the current standard of care for COVID patients, or in combination or alternation with any other compound or therapy that the healthcare provider deems beneficial for the patient. The combination and/or alternation therapy can be therapeutic, adjunctive or palliative.

It has been observed that COVID patients can pass through various stages of disease, and that the standard of care can differ based on what stage of illness the patient presents with or advances to. COVID is noteworthy for the development of "cross-talk" between the immune system and the coagulation system. As the disease progresses, the patient can mount an overreaction by the immune system, which can lead to a number of serious implications, including a cytokine storm. Via the cross-talk between the immune system and the coagulation system, the patient can begin clotting in various areas of the body, including the respiratory system, brain, heart and other organs. Multiple clots throughout the body have been observed in COVID patients, requiring anticoagulant therapy. It is considered that these clots may cause long term, or even permanent damage if not treated and disease alleviated.

More specifically, COVID-19 has been described as progressing through four general stages of illness: stage 1 (early infection), stage 2 (pulmonary phase), stage 3 (hyperinflammation phase/cytokine storm) and stage 4 (long-term sequelae—persisting after the typical convalescence period).

Stage 1 is characterized by non-specific and often mild symptoms. Viral replication is occurring, and it is appropriate to begin immediate treatment with the compounds described herein and perhaps in combination or alternation with another anti-viral therapy. Interferon-β may also be administered to augment the innate immune response to the virus. In one embodiment, therefore, a compound of Formula (I) or a pharmaceutically acceptable salt thereof is used in an effective amount in combination or alternation with interferon-β and or an additional anti-viral drug. Zinc supplements and or Vitamin C is also sometimes administered at this stage or as the illness progresses.

Stage 2 of COVID-19 is the pulmonary phase where patients may experience acute hypoxemic respiratory failure. In fact, the primary organ failure of COVID-19 is hypoxemic respiratory failure. It has been shown that moderate immunosuppression via a steroid, for example, dexamethasone, can be beneficial to patients with acute hypoxemic respiratory failure and/or patients on mechanical ventilation. In one embodiment, a compound of Formula (I) or a pharmaceutically acceptable salt thereof is used in an effective amount in combination with a corticosteroid which may be a glucocorticoid. Non-limiting examples are budesonide, betamethasone, prednisone, prednisolone, triamcinolone, methylprednisolone, hydrocortisone, fludrocortisone acetate, deoxycorticosterone acetate, aldosterone, beclometasone or dexamethasone.

Stage 3, the final stage of the disease, is characterized by progressive disseminated intravascular coagulation (DIC), a condition in which small blood clots develop throughout the bloodstream. This stage also can include multi-organ failure (e.g. vasodilatory shock, myocarditis). It has also been observed that many patients respond to this severe stage of COVID-19 infection with a "cytokine storm". There does appear to be a bidirectional, synergistic relationship between DIC and cytokine storm. To combat DIC, patients are often administered an anti-coagulant agent, which may, for example, be an indirect thrombin inhibitor or a direct oral anticoagulant ("DOAC"). Non-limiting examples are low-molecular weight heparin, warfarin, bivalirudin, rivaroxaban, dabigatran, apixaban or edoxaban. In one embodiment, a compound of Formula (I) or a pharmaceutically acceptable salt thereof is administered in combination or in alternation with anti-coagulant therapy. In some severe cases of clotting in COVID patients, TPA can be administered (tissue plasminogen activator).

It has been observed that high levels of the cytokine interleukin-6 (IL-6) are a precursor to respiratory failure and death in COVID-19 patients. To treat this surge of an immune response, which may constitute a cytokine storm, patients can be administered an IL-6-targeting monoclonal antibody, pharmaceutical inhibitor or protein degrader such as a bispecific compound that binds to IL-6 and also to a protein that mediates degradation. Examples of antibodies include tocilizumab, sarilumab, siltuximab, olokizumab and clazakizumab. In one embodiment, a compound of Formula (I) or a pharmaceutically acceptable salt thereof is administered in combination or in alternation with tocilizumab or sarilumab. Additional nonlimiting examples of immunosuppressant drugs used to treat the overreacting immune system include Janus kinase inhibitors (tofacitinib, baricitinib, filgotinib); calcineurin inhibitors (cyclosporine), tacrolimus, mTOR inhibitors (sirolimus, everolimus) and IMDH inhibitors (azathioprine). Additional antibodies and biologics include abatacept, adalimumab, anakinra, certolizumab, etanercept, golimumab, infliximab, ixekizumab, natalizumab, rituximab, secukinumab, tocilizumab, ustekinumab, vedolizumab, basiliximab and daclizumab.

IL-1 blocks the production of IL-6 and other proinflammatory cytokines. COVID patients are also sometimes treated with anti-IL-1 therapy to reduce a hyperinflammatory response, for example, an intravenous administration of anakinra. Anti-IL-1 therapy generally may be for example, a targeting monoclonal antibody, pharmaceutical inhibitor or protein degrader such as a bispecific compound that binds to IL-1 and also to a protein that mediates degradation.

Patients with COVID often develop viral pneumonia, which can lead to bacterial pneumonia. Patients with severe COVID-19 can also be affected by sepsis or "septic shock". Treatment for bacterial pneumonia secondary to COVID or for sepsis includes the administration of antibiotics, for example a macrolide antibiotic, including azithromycin, clarithromycin, erythromycin, or roxithromycin. Additional antibiotics include amoxicillin, doxycycline, cephalexin, ciprofloxacin, clindamycin, metronidazole, sulfamethoxazole, trimethoprim, amoxicillin, clavulanate or levofloxacin. In one embodiment, thus a compound of Formula (I) or a pharmaceutically acceptable salt thereof is administered in combination or in alternation with an antibiotic, for example, azithromycin. Some of these antibiotics such as azithromycin have independent anti-inflammatory properties. Such drugs may be used both as anti-inflammatory agents for COVID patients and have a treatment effect on secondary bacterial infections.

A unique challenge in treating patients infected with COVID-19 is the relatively long-term need for sedation if patients require mechanical ventilation which might last up to or greater than 5, 10 or even 14 days. For ongoing pain during this treatment, analgesics can be added sequentially and for ongoing anxiety, sedatives can be added sequentially. Non-limiting examples of analgesics include acetaminophen, ketamine and PRN opioids (hydromorphone, fentanyl, and morphine). Non-limiting examples of sedatives include melatonin, atypical antipsychotics with sedative-predominant properties (olanzapine, quetiapine), propofol or dexmedetomidine, haloperidol and phenobarbital. In one embodiment, a compound of Formula (I) or a pharmaceutically acceptable salt, a solvate, a solvate of a salt, a hydrate or a polymorph thereof is administered in combination or in alternation with a pain reliever, such as acetaminophen, ketamine, hydromorphone, fentanyl, or morphine. In one embodiment, a compound of Formula (I) a pharmaceutically acceptable salt, a solvate, a solvate of a salt, a hydrate or a polymorph thereof is administered in combination or in alternation with a sedative, such as melatonin, olanzapine, quetiapine, propofol, dexmedetomidine, haloperidol or phenobarbital.

In one embodiment, a compound of the present invention is used in an effective amount in combination with a protease inhibitor such as PF-07304814, PF-00835231, PF-07321332, lopinavir or ritonavir.

In one embodiment, a compound of the present invention is used in an effective amount in combination with a RNA replication modulator such as N4-hydroxycytidine or a prodrug thereof may also be administered. In one special embodiment, the RNA replication modulator is a N4-hydroxycytidine prodrug as described in WO 2019/113462. In one more special embodiment, the RNA replication modulator is molnupiravir.

Additional drugs that may be used in the treatment of a COVID patient include, but are not limited to aspirin, colchicine, dimethyl fumarate, acalabrutinib, favipiravir, fingolimod, methylprednisolone, bevacizumab, tocilizumab, umifenovir, losartan and the monoclonal antibody combination of REGN3048 and REGN3051 or ribavirin. Any of these drugs or vaccines can be used in combination or alternation with an active compound provided herein to treat a viral infection susceptible to such.

In one embodiment, a compound of the present invention is used in an effective amount in combination with anti-coronavirus vaccine therapy, including but not limited to mRNA-1273 (Moderna), AZD-1222 (AstraZeneca and University of Oxford), BNT162b2 (BioNTech), CoronaVac (Sinovac), NVX-CoV 2372 (NovoVax), SCB-2019 (Sanofi and GSK), ZyCoV-D (Zydus Cadila) and CoVaxin (Bharat Biotech). In another embodiment, a compound of the present invention is used in an effective amount in combination with passive antibody therapy or convalescent plasma therapy.

SARS-CoV-2 is constantly mutating, which many increase virulence and transmission rates. Drug-resistant variants of viruses may emerge after prolonged treatment with an antiviral agent. Drug resistance may occur by mutation of a gene that encodes for an enzyme used in viral replication. The efficacy of a drug against an RNA virus infection in certain cases can be prolonged, augmented or restored by administering the compound in combination or alternation with another and perhaps even two or three other, antiviral compounds that induce a different mutation or act through a different pathway, from that of the principle drug. A variant of a known virus can refer to a virus carrying one or more nucleotide mutations in the viral genome as compared to the known virus, for instance at least 1, 2, 3, 4, 5, 6, 7, 8, 9, 10, 15, 20, 30, 40, 60, 100, 200, 300 or even more nucleotide mutations. Mutations can refer to nucleotide deletion, insertion, or substitution. In some cases, a variant can have at most 50%, 40%, 30%, 20%, 10%, 5%, 4%, 3%, 2% or 1% of the viral genome different than the genome of a known virus.

Alternatively, the pharmacokinetics, biodistribution, half-life or other parameter of the drug can be altered by such combination therapy (which may include alternation therapy if considered concerted).

Examples of other therapeutic agents that may be combined with a compound of Formula (I) or a pharmaceutically acceptable salt, a solvate, a solvate of a salt, a hydrate or a polymorph thereof, either administered separately, or in the same pharmaceutical composition include, but are not limited to a:

(1) Protease inhibitor;
(2) Polymerase inhibitor;
(3) Allosteric polymerase inhibitor;
(4) Interferon alfa-2a, which may be pegylated or otherwise modified, and/or ribavirin;
(5) Non-substrate-based inhibitor;
(6) Helicase inhibitor;
(7) Primase-helicase inhibitor;
(8) Antisense oligodeoxynucleotide (S-ODN);
(9) Aptamer;
(10) Nuclease-resistant ribozyme;
(11) iRNA, including microRNA and SiRNA;
(12) Antibody, partial antibody or domain antibody to the virus;
(13) Viral antigen or partial antigen that induces a host antibody response;
(14) NOD-, LRR- and pyrin domain-containing protein 3 (NLRP3); or
(15) other DHODH inhibitors (e.g. brequinar, teriflunomide, leflunomide, PTC299, MEDS433, AG-636, ASLAN003, JNJ-74856665, RP7214, PP-001 and BAY2402234).

In another preferred of the method according to the present invention, said prevention and/or treatment is in combination with other DHODH inhibitors (e.g. as described herein), and/or standard antiviral therapy (SAT), for example selected from at least one of neuraminidase inhibitors (e.g. oseltamivir, zanamivir), favipiravir, remdesivir, ribavirin (tribavirin), interferon alfa-2b/ribavirin systemic, interferon alpha 2a or 2b, inclusive any pegylated versions, chloroquine or hydroxychloroquine (given in combination with azithromycin), dolutegravir+rilpivirine (JULUCA®), dolutegravir+lamivudine (DOVATO®), ritonavir+lopinavir (KALETRA®), bictegravir+tenofovir alafenamide+emtricitabine (BIKTARVY®), dolutegravir+abacavir+lamivudine (TRIUMEQ®), elvitegravir+cobicistat+emtricitabine+tenofovir alafenamide (GENVOYA®), and elvitegravir+cobicistat+emtricitabine+tenofovir disoproxil fumarate+emtricitabine (STRIBILD®). Preferred are combinations with remdesivir, chloroquine or hydroxychloroquine.

In more preferred of the method according to the present invention, the combinations is: DHODH inhibitors (e.g. as described herein) with at least remdesivir, chloroquine or hydroxychloroquine, more preferably IMU-838+remdesivir, chloroquine or hydroxychloroquine.

One embodiment regarding the method of preventing and/or treating is in combination with standard antiviral therapy (SAT), which comprises at least remdesivir.

In a special embodiment, the combination is the "Polymorph A" of IMU-838 with remdesivir.

Preferred is the method with the combination with other DHODH inhibitors (e.g. as described herein), and/or standard antiviral therapy (SAT), for use according to the present invention, wherein said viral infection is caused by an RNA virus. RNA viruses can be single-stranded or double-stranded, and preferably include viruses that cause diseases in mammals, such as the human.

Preferable examples are HIV, HCV, Ebola, rotavirus, Zika virus, polio virus, rhinovirus, hepatitis A virus, measles virus, mumps virus, RSV, rabies, Lassa virus, hantavirus, or influenza, in particular a single stranded RNA virus, such as HCoV-229E, HCoV-NL63, or betacoronaviruses, such as HCoV-OC43, SARS-CoV-1, HCoV-HKU1, MERS-CoV or SARS-CoV-2, which is particularly preferred. A more preferred combination for use according to the present invention is DHODH inhibitors (e.g. as described herein) with at least remdesivir, chloroquine or hydroxychloroquine, more preferably IMU-838+at least remdesivir, chloroquine or hydroxychloroquine for betacoronaviruses infection, in particular SARS-CoV-2.

In another aspect of the present invention, in the preferred method using the combination with standard antiviral therapy (SAT), the ratio of an effective amount of DHODH inhibitors to an effective amount of standard antiviral therapy (SAT), also referred herein as DHODH inhibitors/SAT, is from 0.1 to 10, more preferably from 0.2 to 10, more preferably from 0.2 to 1 or from 1 to 10. A more preferred ratio for the combination of IMU-838+at least remdesivir is 10 or 0.2.

In the method, the compound for use can be provided and/or is administered as a suitable pharmaceutical composition as discussed above. The compounds can be administered alone or in combination with other active compounds—for example with medicaments already known for the treatment of the aforementioned diseases, whereby in the latter case a favorable additive, amplifying or preferably synergistically effect is noticed. Suitable amounts and dosages to be administered to mammals, in particular humans, are as above, and can range from 5 to 500 mg, in particular 10 mg to 100 mg.

Preferred is a method according to the present invention, wherein said method of preventing and/or treating is in combination with other DHODH inhibitors, and/or standard antiviral therapy (SAT), for example selected from at least one of neuraminidase inhibitors (e.g. oseltamivir, zanamivir), favipiravir, remdesivir, ribavirin (tribavirin), interferon alfa-2b/ribavirin systemic, interferon alpha 2a or 2b, inclusive any pegylated versions, chloroquine or hydroxychloroquine (given in combination with azithromycin), dolutegravir+rilpivirine (JULUCA®), dolutegravir+lamivudine (DOVATO®), ritonavir+lopinavir (KALETRA®), bictegravir+tenofovir alafenamide+emtricitabine (BIKTARVY®), dolutegravir+abacavir+lamivudine (TRIUMEQ®), elvitegravir+cobicistat+emtricitabine+tenofovir alafenamide (GENVOYA®), and elvitegravir+cobicistat+emtricitabine+tenofovir disoproxil fumarate+emtricitabine (STRIBILD®). Preferred are combinations with remdesivir, chloroquine or hydroxychloroquine.

In a preferred embodiment of the method according to the present invention, the compound is administered to said subject in an effective dosage, for example of 45 mg daily, taken as 22.5 mg BID in the morning 15-60 min before a meal, and in the evening at least 2 hours after any meal. It is desirable to reach a plasma level of the compound for use of between 0.1 to 50 µM.

In the context of the method of the present invention, it was surprisingly found that the compound vidofludimus shows particular advantages both in the prevention of viral infection as well as in the treatment of later stages of the diseases, particularly as a combination treatment.

In the preventive approach of the method according to the present invention, the compound can be administered to a subject immediately after detection of infection.

In the preventive approach of the method according to the present invention, the compound can be administered to a subject "late" and is still effective, e.g. when administered at between 8 to 24 hours post infection, preferably at between 10 to 20 hours post infection, more preferably at 12 to 16 hours post infection. This regimen still provides a surprisingly low viral load.

In the treatment approach of the method according to the present invention, the compound can be administered to a subject immediately post infection.

In the treatment approach of the method according to the present invention, the compound can be administered to a subject "late" in the infection cycle, and is still effective, in particular as a (synergistic) combination therapy, e.g. when administered at between 5 to 14 days post infection, preferably at between 5 to 11 days post infection, more preferably at 7 to 11 days post infection. This regimen provides a surprisingly effective treatment effect, and furthermore helps to control excessive immune reactions, like cytokine storms.

In the preventive approach, the compound can also be administered prophylactically to prevent an infection with coronaviruses or reduce the reproduction of coronaviruses.

In a further embodiment of the method according to the present invention, the compound is administered to a subject for 14 days or more.

In a preferred embodiment of the method according to the present invention, the compound is administered to a subject for 14 days.

The present invention will now be described further in the following examples with reference to the accompanying Figures, nevertheless, without being limited thereto. For the purposes of the present invention, all references as cited herein are incorporated by reference in their entireties.

With the above context, specific embodiments of the invention are represented by the below consecutively numbered embodiments:

1. A compound according to Formula (I),

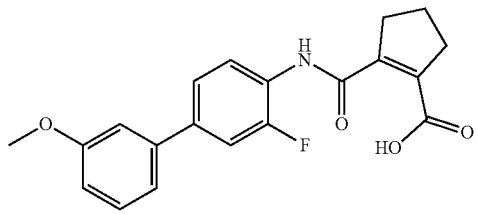

Formula (I)

an organic acid derivative thereof, a physiologically acceptable salt, a solvate, a hydrate or a polymorph thereof for use in the prevention and/or treatment of diseases caused by viral infection in a mammalian subject, such as a human.

2. The compound for use according to embodiment 1, wherein said viral infection is by an RNA virus, such as, for example HIV, HCV, Ebola, rotavirus, Zika virus, polio virus, rhinovirus, hepatitis A virus, measles virus, mumps virus, RSV, rabies, Lassa virus, hantavirus, or influenza, in particular a single stranded RNA virus, such as HCoV-229E, HCoV-NL63, or betacoronaviruses, such as HCoV-OC43, SARS-CoV-1, HCoV-HKU1, MERS-CoV or SARS-CoV-2.

3. The compound for use according to embodiment 1 or 2, wherein said disease is selected from AIDS, hepatitis, ebola, polio, diarrhea, measles, mumps, rabies, Lassa fever, viral flu, respiratory disease, acute respiratory disease, sepsis, acute respiratory distress syndrome, and adverse immune reactions, in particular moderate to severe cases of said diseases, and wherein said disease preferably is selected from diseases causes by SARS-CoV-2, in particular COVID-19, such as acute respiratory disease, sepsis, acute respiratory distress syndrome, and adverse immune reactions, such as a cytokine storm.

4. The compound for use according to any one of embodiments 1 to 3, wherein said prevention and/or treatment is in combination with other DHODH inhibitors, and/or standard antiviral therapy (SAT), for example selected from at least one of neuraminidase inhibitors (e.g., oseltamivir, zanamivir), favipiravir, remdesivir, ribavirin (tribavirin), interferon alfa-2b/ribavirin systemic, interferon alpha 2a or 2b, inclusive any pegylated versions, chloroquine or hydroxychloroquine (given in combination with azithromycin), dolutegravir+rilpivirine (JULUCA®), dolutegravir+lamivudine (DOVATO®), ritonavir+lopinavir (KALETRA®), bictegravir+tenofovir alafenamide+emtricitabine (BIKTARVY®), dolutegravir+abacavir+lamivudine (TRIUMEQ®), elvitegravir+cobicistat+emtricitabine+tenofovir alafenamide (GENVOYA®), and elvitegravir+cobicistat+emtricitabine+tenofovir disoproxil fumarate+emtricitabine (STRIBILD®).

5. The compound for use according to embodiment 4, wherein standard antiviral therapy (SAT) comprises at least remdesivir.

6. The compound for use according to any one of embodiments 4 or 5 wherein the ratio of an effective amount of DHODH inhibitors to an effective amount of standard antiviral therapy (SAT), also referred herein as DHODH inhibitors/SAT, is from 0.1 to 10, from 0.2 to 10, from 0.2 to 1 or from 1 to 10.

7. The compound for use according to any one of embodiments 1 to 6, wherein said compound is provided as a suitable pharmaceutical composition, such as a tablet, capsule, granule, powder, sachet, reconstitutable powder, dry powder inhaler and/or chewable.

8. The compound for use according to any one of embodiments 1 to 7, wherein said compound is administered to said subject in an effective dosage, for example of 45 mg daily, taken as 22.5 mg BID in the morning 15-60 min before a meal, and in the evening at least 2 hours after any meal.

9. The compound for use according to any one embodiments 1 to 8, wherein said compound is administered to said subject at between 5 to 14 days post infection, preferably at between 5 to 11 days post infection, more preferably at 7 to 11 days post infection.

10. The compound for use according to any one embodiments 1 to 8, wherein for prevention said compound is administered to said subject at between 8 to 24 hours post infection, preferably at between 10 to 20 hours post infection, more preferably at 12 to 16 hours post infection.

11. The compound for use according to any one embodiments 1 to 10, wherein said prevention and/or treatment further comprises monitoring in said subject of at least one biomarker selected from the group of mean viral load, qualitative virological clearance of nasopharyngeal or respiratory samples using RT PCR test, D-dimer, LDH, C-reactive protein (CRP), IL-17, IFN-γ, IL-1ß, IL-6, TNFa, seroconversion, and IgM and IgG neutralizing antibodies.

12. A method for preventing and/or treating viral infection in a mammalian subject, such as a human, comprising administering to said mammal an effective amount of a compound according to Formula (I), Formula (I)

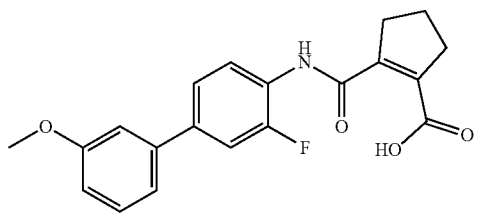

an organic acid derivative thereof, a physiologically acceptable salt, a solvate, a hydrate or a polymorph thereof.

13. The method according to embodiment 12, wherein said viral infection is by an RNA virus, such as, for example HIV, HCV, Ebola, rotavirus, Zika virus, polio virus, rhinovirus, hepatitis A virus, measles virus, mumps virus, RSV, rabies, Lassa virus, hantavirus, or influenza, in particular a single stranded RNA virus, such as HCoV-229E, HCoV-NL63, or betacoronaviruses, such as HCoV-OC43, SARS-CoV-1, HCoV-HKU1, MERS-CoV or SARS-CoV-2.

14. The method according to embodiment 12 or 13, wherein said method of preventing and/or treating is in combination with other DHODH inhibitors, and/or standard antiviral therapy (SAT), for example selected from at least one of neuraminidase inhibitors (e.g., oseltamivir, zanamivir), favipiravir, remdesivir, ribavirin (tribavirin), interferon alfa-2b/ribavirin systemic, interferon alpha 2a or 2b, inclusive any pegylated versions, chloroquine or hydroxychloroquine (given in combination with azithromycin), dolutegravir+rilpivirine (JULUCA®), dolutegravir+lamivudine (DOVATO®), ritonavir+lopinavir (KALETRA®), bictegravir+tenofovir alafenamide+emtricitabine (BIKTARVY®), dolutegravir+abacavir+lamivudine (TRIUMEQ®), elvitegravir+cobicistat+emtricitabine+tenofovir alafenamide (GENVOYA®), and elvitegravir+cobicistat+emtricitabine+tenofovir disoproxil fumarate+emtricitabine (STRIBILD®).

15. The method according to embodiment 14, wherein standard antiviral therapy (SAT) comprises at least remdesivir.

16. The method according to any one of embodiments 14 or 15 wherein the ratio of an effective amount of DHODH inhibitors to an effective amount of standard antiviral therapy (SAT), also referred herein as DHODH inhibitors/SAT, is from 0.1 to 10, from 0.2 to 10, from 0.2 to 1 or from 1 to 10.

17. The method according to any one of embodiments 12 to 16, wherein said compound is administered to said subject in an effective dosage, for example of 45 mg daily, taken as 22.5 mg BID in the morning 15-60 min before a meal, and in the evening at least 2 hours after any meal.

18. The method according to any one of embodiments 12 to 17, wherein said compound is administered to said subject at between 5 to 14 days post infection, preferably at between 5 to 11 days post infection, more preferably at 7 to 11 days post infection.

19. The method according to any one of embodiments 12 to 17, wherein for prevention said compound is administered to said subject at between 8 to 24 hours post infection, preferably at between 10 to 20 hours post infection, more preferably at 12 to 16 hours post infection.

20. A method of treating a viral infection in a subject in need thereof, the method comprising administering to the subject a therapeutically-effective amount of a DHODH inhibitor of structure

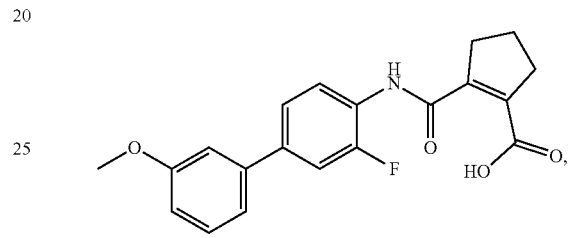

a pharmaceutically acceptable salt, a solvate, a solvate of a salt, a hydrate or a polymorph thereof, wherein the viral infection is caused by a coronavirus.

21. The method of embodiment 20, wherein the coronavirus is a betacoronavirus.

22. The method of embodiment 20 or embodiment 21, wherein the coronavirus is SARS-CoV-2.

23. The method of embodiment 20, wherein the DHODH inhibitor is the pharmaceutically-acceptable salt, wherein the pharmaceutically-acceptable salt is a calcium salt.

24. The method of any one of embodiments 20-23, wherein the DHODH inhibitor is administered to the subject twice a day for at least two weeks.

25. The method of any one of embodiments 20-23, wherein the DHODH inhibitor is administered to the subject twice a day for at least about two weeks, and wherein the DHODH is administered at least about 15 minutes to about 60 minutes before a meal for each administration.

26. The method of any one of embodiments 20-25, wherein the DHODH inhibitor is administered to the subject between from about 5 days to about 14 days after infection with the coronavirus.

27. The method of any one of embodiments 20-27, wherein the DHODH inhibitor is formulated for oral administration.

28. The method of any one of embodiments 20-27, wherein the DHODH inhibitor is administered to the subject as a tablet.

29. The method of any one of embodiments 20-28, wherein the therapeutically-effective amount of the DHODH inhibitor is from about 20 mg to about 50 mg.

30. The method of any one of embodiments 20-29, wherein the therapeutically-effective amount of the DHODH inhibitor is about 45 mg.

31. The method of any one of embodiments 20-30, wherein the therapeutically-effective amount of the DHODH inhibitor is about 22.5 mg of the DHODH inhibitor two times per day.

32. The method of any one of embodiments 20-31, wherein the viral infection causes the subject to have a cytokine storm.

33. The method of any one of embodiments 20-32, further comprising administering to the subject a therapeutically-effective amount of an additional therapeutic agent.

34. The method of embodiment 33, wherein the additional therapeutic agent is remdesivir.

35. A method of providing therapy for a viral infection in a subject in need thereof, the method comprising administering to the subject a therapeutically-effective amount of a DHODH inhibitor of structure

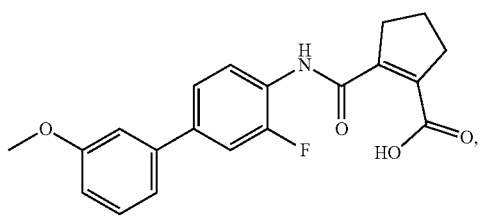 [SMILES: COc1cccc(-c2ccc(NC(=O)C3=C(C(=O)O)CCC3)c(F)c2)c1]

a pharmaceutically acceptable salt, a solvate, a solvate of a salt, a hydrate or a polymorph thereof, wherein the viral infection is caused by a coronavirus.

Examples

Background

IMU-838 is a small molecule investigational drug (vidofludimus calcium) under development as an oral tablet formulation for the treatment of relapsing-remitting multiple sclerosis (RRMS), inflammatory bowel disease (IBD) and other chronic inflammatory and autoimmune diseases.

Initial clinical trials were also conducted using a free acid formulation of the active moiety of IMU-838 (vidofludimus) as an amorphous material. In total, this clinical trial data encompasses more than 250 patients treated with the active moiety, helping generate a safety database to encourage further development of IMU-838. Results were generated supporting tolerability of repeated daily dosing of up to 50 mg of IMU-838.

Given the independence of the antiviral effect with respect to virus specific proteins and their structure, DHODH inhibition seems broadly applicable to several viruses. Such broad-spectrum antiviral effects have been observed in various virus infected cells, such as influenza virus infections, cytomegalovirus infections and even hemorrhagic fever-causing viruses, such as Lassa virus. Therefore, the results as discussed in the present examples using the compounds having improved pharmaceutical properties can be readily extrapolated to RNA-viruses, such as SARS-CoV-2 infections.

Preliminary experiments (e.g. WO2012/128050 or Kim et al. in *Viruses* 2020; 12:821) have demonstrated that IMU-838 has broad-spectrum antiviral activity at concentrations achieved in the blood of treated patients (plasma levels 10 to 30 µM). The antiviral activity of IMU-838 against HIV and hepatitis C virus (HCV) was tested in cell culture experiments. It was shown that IMU-838 inhibited the viral replication. In another series of experiments, human peripheral blood mononuclear cells (PBMCs), seronegative for HIV and hepatitis B virus, were infected in vitro with HIV-191US005 (CCR5-tropic, Subtype B). Reverse transcriptase activity and the appearance of the specific HIV antigen p24 were evaluated at different IMU-838 concentrations. The median effective dose ($ED_{50}$) was approximately 2 µM. IMU-838 was also evaluated in a Huh7 human hepatoma cell line harboring an HCV sub genomic replicon of genotype 1b with a stable luciferase (Luc) reporter and three cell culture-adaptive mutations. HCV replicon levels were assessed with the replicon-derived Luc activity as readout at different concentrations of IMU-838. The median $ED_{50}$ was 4.6 µM.

Finally, in cellular A549 and Vero models of mammalian Arena virus infections, the RNA virus causing human hemorrhagic fever diseases like Lassa fever, IMU-838 demonstrated activity with an $IC_{50}$ (the concentration of drug that inhibits 50% of the activity of the target) of 2.8 µM. In addition, it was shown that, in this case, DHODH inhibition mediated effects against this virus type are independent of IFN signaling.

TABLE 1

IMU-838 is broadly active against various RNA and DNA viruses

| | IMU-838 $IC_{50}$ | Test System |
|---|---|---|
| hDHODH | 0.12 µM | In vitro, protein, human |
| mDHODH | 10.0 µM | In vitro, protein, mouse |
| Cytotoxicity on fibroblasts | >30 µM | Cellular |
| Cytotoxicity on HepG2 cells | >50 µM | Cellular |
| HIV | 2.2 µM | RT (reverse transcriptase) |
| | 2.0 µM | p24 |
| HCV | 4.6 µM | Replicon, luciferase |
| Lassa fever Arena virus | 2.8 µM | Plaque reduction, virus protein expression |

Secondary activation of the innate immune response has also been described as a relevant downstream mechanism. Therefore, DHODH inhibition ameliorates and blocks the viruses' ability to "hijack" the human host cell mechanisms of RNA production as a means to virus replication. This is a host cell mechanism with the advantage of broad viral activity, is not influenced by resistances or mutations of the virus and can be combined with other antiviral drugs targeting the virus itself.

Preparation of Test Compounds

There are various possibilities to produce the compounds of Formula (I), such as the method described in JP-A-50-121428, WO 2012/001148 (example 4), or Kralik et al. SAR, species specificity, and cellular activity of cyclopentene dicarboxylic acid amides as DHODH inhibitors, Bioorganic & Medicinal Chemistry Letters, Volume 15, Issue 21, 1 Nov. 2005, Pages 4854-4857, incorporated herein by reference.

In particular the following methods of synthesis were used.

Method 1: In a first step the cycloalkene-1,2-dicarboxic acids can be obtained from the corresponding α,α'-dibromo alkanedicarboxylic acids as described by R. N. Mc Donald and R. R. Reitz, J. Org. Chem. 37, (1972) 2418-2422. Cyclopentene-1,2-dicarboxylic acid can also be obtained in large amounts from pimelic acid [D. C. Owsley and J. J. Bloomfield, Org. Prep. Proc. Int. 3, (1971) 61-70; R. Willstätter, J. Chem. Soc. (1926), 655-663]. Dicarboxylic acids substituted in or on the ring system can be synthesized in general via the cyanhydrine synthesis [Shwu-Jiüan Lee et. al., Bull. Inst. Chem. Academia Sinica Number 40, (1993), 1-10 or B. R. Baker at al., J. Org. Chem. 13, 1948, 123-133; and B. R. Baker at al., J. Org. Chem. 12, 1947, 328-332; L. A. Paquette et. al., J. Am. Chem. Soc. 97, (1975), 6124-

6134]. The dicarboxylic acids can then be converted into the corresponding acid anhydrides by reacting them with acetic acid anhydride [P. Singh and S. M. Weinreb, Tetrahedron 32, (1976), 2379-2380].

Other methods for preparing different acid anhydrides are also described in V. A. Montero at al., J. Org. Chem. 54, (1989), 3664-3667; P. ten Haken, J. Heterocycl. Chem. 7, (1970), 1211-1213; K. Alder, H. Holzrichter, J. Lieb. Annalen d. Chem. 524, (1936), 145-180; K. Alder, E. Windemuth, J. Lieb. Annalen d. Chem. 543, (1940), 56-78; and W. Flaig, J. Lieb. Annalen d. Chem. 568, (1950), 1-33.

These anhydrides may then be reacted with the corresponding amines to the desired amides of Formula (I). This reaction can be carried out either by use of the reaction conditions as described in J. V. de Julian Ortiz et al., J. Med. Chem. 42, (1999), 3308 (designated route A in Example 1) or by use of 4-dimethylamino pyridine (designated route B in Example 1).

Method 2: The amides of Formula (I) can also be synthesized by reacting an amine of the formula (IV) with an arylboronic-acid of the general formula (V) [M. P. Winters, Tetrahedron Lett., 39, (1998), 2933-2936]. Biarylaniline can be synthesized in general via the palladium coupling [G. W. Kabalka et al., Chem. Commun., (2001), 775; A. Demeter, Tetrahedron Lett. 38; (1997), 5219-5222; V. Snieckus, Chem. Commun. 22, (1999), 2259-2260].

Method 3: The amides of Formula (I) can also be synthesized by reacting an halogen derivative of the formula (VI) with an arylboronic acid of the general formula (VII) [N. E. Leadbeater, S. M. Resouly, Tetrahedron, 55, 1999, 11889-11894].

Preparation of the calcium salts: The synthesis of the calcium salts of compounds of Formula (I) is described in detail in WO 2012/001148, which is incorporated herein by reference.

WO 2019/175396 describes a new white crystalline calcium salt (Formula (II), designated as "Polymorph A"), which are incorporated herein by reference. The two calcium polymorphs can be distinguished via their X-ray powder diffraction (XRPD) pattern:

(a) the yellowish calcium polymorph as shown in FIG. 5 from WO 2012/001148;

(b) the white calcium polymorph according Formula (II), designated as "Polymorph A", as shown in FIG. 1 from WO 2019/175396.

Assays and Testing
Proliferation Assay of Human T-Cells

Human peripheral blood mononuclear cells (PBMCs) were obtained from healthy volunteers and transferred to RPMI1640 cell culture medium containing 10% dialyzed fetal calf serum. 80.000 cells per well were pipetted into a 96-well plate and phytohemagglutinin (PHA) was added in phosphate buffered saline to a final concentration of 20 µg/ml to stimulate T-cell proliferation. Vidofludimus was added in dimethyl sulfoxide (DMSO, final concentration: 0.1 vol %) to final concentrations ranging from 20 nM to 50 µM. After incubation for 48 hours, cell proliferation was quantified using the "cell proliferation ELISA BrdU" (Roche) according to the manufacturer's instructions. Half maximal inhibition ($IC_{50}$) was calculated using a 4-parameter sigmoidal curve fit. T-cell proliferation was inhibited by vidofludimus with an $IC_{50}$ of 4.1 µM.

Determination of Bioavailability

Oral bioavailabilities of the calcium salt and the free acid of vidofludimus were compared in male Wistar rats. The free acid or the calcium salt was filled into gelatin capsules and the animals received a single administration at a dose level of approximately 10 mg free acid equivalents per kilogram body weight.

Four male Wistar rats (body weight range: 250-275 g) per group were treated with either vidofludimus free acid or its calcium salt. The capsules were administered into the esophagus of the animals using an application device. Venous blood samples were taken from the animals under isoflurane anesthesia at the following time points after administration: 30 min; 1 h; 2 h; 4 h; 6 h; 8 h; 24 h; 28 h; 32 h and 48 h. Coagulation was inhibited using Na-heparin and plasma was generated by centrifugation of the blood samples. Plasma samples were analyzed for vidofludimus by LC-MS/MS and pharmacokinetic parameters were calculated according to the mixed log linear trapezoidal method.

To examine the potassium salt, six female Lewis rats (body weight ca. 200 g) were treated with either vidofludimus free acid or its potassium salt at a dose level of 30 mg/kg (free acid equivalents). The compounds were formulated in 0.5% methylcellulose in phosphate buffered saline and the animals were treated by oral gavage. Venous blood samples were taken from the animals under isoflurane anesthesia at the following time points after administration: 30 min; 1 h; 2 h; 4 h; 8 h; 26 h; 33 h; 48 h and 72 h. Coagulation was inhibited using Na-heparin and plasma was generated by centrifugation of the blood samples. Plasma samples were analyzed for vidofludimus by LC-MS/MS and pharmacokinetic parameters (AUC) were calculated according to the linear trapezoidal rule method.

Oral bioavailabilies of the salts were evaluated by comparing the areas under the plasma-concentration-time-curves (AUCs) and the maximally attained plasma concentrations (Cmax values) of vidofludimus after administration of the salt with those observed after administration of the free acid. These ratios are shown in Table 2.

TABLE 2

Comparison of PK parameters after oral application of vidofludimus to rats

| Compound | $AUC_{inf}/AUC_{inf, free\ acid}$ | $C_{max}/C_{max,\ free\ acid}$ |
|---|---|---|
| Vidofludimus free acid | 1 | 1 |
| Potassium salt | 0.96 | 1.09 |
| Calcium alt | 1.72 | 1.67 |

In Vitro Test of IMU-838 for Antiviral Activity Against SARS-CoV-2

IMU-838 was tested for in vitro antiviral activity against SARS-CoV-2 using Vero 76 cells. Test media was MEM with 2% FBS and gentamicin.

The virus was prepared in test media to achieve the lowest possible multiplicity of infection (MOI) that would yield >80% cytopathic effect (CPE) within 5 days. Plates were infected prior to preparation and addition of compound as described below. The MOI for this study was 0.002.

The compound was received in powder form, and was solubilized in DMSO to prepare a 100 mM stock solution. Compound was then serially diluted using eight half-log dilutions in DMSO and finally diluted in test medium, so that the starting (high) test concentration was 100 µM. Each dilution was added to 5 wells of a 96-well plate with 80-100% confluent cells. Three wells of each dilution were infected with virus, and two wells were uninfected as toxicity controls. Six wells were infected and untreated as virus controls, and six wells were uninfected and untreated as cell controls. M128533 (protease inhibitor) was tested in parallel as a positive control. Plates were incubated at 37±2° C., 5% $CO_2$.

For virus yield reduction assays, the supernatant fluid from each compound concentration was collected on day 3 post infection (3 wells pooled) and virus titer was quantified using a standard endpoint dilution $CCID_{50}$ assay and titer calculations using the Reed-Muench (1948) equation. The concentration of compound required to reduce virus yield by 1 log 10 was calculated by regression analysis.

On day 5 post-infection, once untreated virus control wells reached maximum CPE, plates were stained with neutral red dye for approximately 2 hours (±15 minutes). Supernatant dye was removed and wells rinsed with PBS, and the incorporated dye was extracted in 50:50 Sorensen citrate buffer/ethanol for >30 minutes and the optical density was read on a spectrophotometer at 540 nm. Optical densities were converted to percent of cell controls and normalized to the virus control, then the concentration of test compound required to inhibit CPE by 50% ($EC_{50}$) was calculated by regression analysis. The concentration of compound that would cause 50% cell death in the absence of virus was similarly calculated (COO. The selective index (SI) is the $CC_{50}$ divided by $EC_{50}$.

Antiviral results are shown in Table 3. IMU-838 exhibited antiviral activity against SARS-CoV-2 at concentrations between 0.32 to 10 µM. The positive control compound also performed as expected.

TABLE 3

In vitro antiviral activity of IMU-838 against coronavirus SARS-CoV-2

| | $EC_{50}$ | $CC_{50}$ | SI |
|---|---|---|---|
| IMU-838 | 6.1 | 7.9 | 1.3 |

Units are in µM
$EC_{50}$: 50% effective antiviral concentration
$CC_{50}$: 50% cytotoxic concentration of compound without virus added
SI=$CC_{50}/EC_{50}$ The inhibitory efficacy of IMU-838 on SARS-CoV-2-infected cells was further validated using variable read-out methods in several cell lines and lineages (Hahn et al. *Viruses* 2020; 12:1394). lineages. SARS-CoV-2-infected, drug-treated CaCo-2 cells were used for the transfer of supernatants to monolayers of Vero E6 cells for the quantitation of plaque formation and in this approach a 58-fold reduction of viral plaques was observed for the treatment setting. Moreover, performing a VYR assay with Vero 76 cells, a virus-specific $EC_{90}$ of 6.2±1.9 µM was measured, with no cytotoxicity observed with drug concentrations up to 100 µM at 3 days post infection. Table 4 gives an overview.

The inhibitory efficacy of IMU-838 in mutated SARS-CoV-2 strains can be determined similar: IMU-838 was tested in addition to the SARS-CoV-2 wild type or original Wuhan strain in the variants of concern B.1.1.7 and B.1.351 in a virus yield reduction assay similarly performed as described above. Vero E6 cells were pretreated for 24 h with different concentrations of IMU-838, virus was added for 48 h and subsequently supernatants were harvested to determine the $CCID_{50}$. IMU-838's dose-dependent reduction of infectivity was demonstrated for all three variants with an even stronger log unit reduction in the variants of concern (at 10 µM>3 log units) compared to the original Wuhan strain (at 10 µM~2 log units).

Test of Activity and Safety of Vidofludimus in Human Patients

A 14-day, phase 2, two-group, multicenter, randomized, placebo-controlled, double-blinded clinical trial in patients with acute SARS-CoV-2 infection and clinical symptoms is performed. IMU-838 versus placebo is tested on the background of standard-of-care treatment available in both treatment arms, namely Arm 1: 2×22.5 mg IMU-838+standard-of-care
Arm 2: 2×placebo+standard-of-care IMU-838 and placebo are provided as small (diameter of 8 mm) white tablets for oral use.

Formulation: Tablets with 22.5 mg IMU-838, round, 8 mm diameter in size, uncoated Administration: Tablets are taken twice daily, in the morning 15-60 min before a meal, and in the evening at least 2 hours after any meal and 15-60 min before any meal Dose: 45 mg (taken as 22.5 mg BID)

Reference product: Matching placebo, administration as described for the test product Inclusion criteria are patients fulfilling category 3-4 of the clinical status as assessed with the nine-category ordinal scale proposed by the WHO COVID-19 Therapeutic Trial Synopsis (www.who.int/publications/i/item/covid-19-therapeutic-trial-synopsis) as well as additional standard clinical and laboratory conditions.

The primary clinical endpoint is assessed by the proportion of patient that require invasive ventilation during the study period, i.e. the superiority of IMU-838 plus standard of care (SOC) vs. placebo plus SOC in adult subjects with Covid-19 regarding time to clinical improvement or hospital discharge is evaluated.

Further secondary outcome measures include time to improvement of clinical status, need for extracorporeal membrane oxygenation (ECMO) or renal-replacement therapy during and after 28 days, and the duration and need to treat the patient within an intensive care unit (ICU), comparing treatment with IMU-838 plus SOC vs. placebo plus SOC; 28-day all-cause mortality in this COVID-19 patient population comparing treatment with IMU-838 plus SOC vs. placebo plus SOC; and to evaluate safety and tolerability of IMU-838 plus SOC vs. placebo plus SOC in

TABLE 4

Overview of IMU-838 efficacy in cultured-cell-based SARS-CoV-2 infection models

| Cells | SARS-CoV-2 isolate | MOI | Assay | $EC_{50}$ [µM] | $CC_{50}$ [µM] | $SI_{50}$ | $EC_{90}$ [µM] | $CC_{90}$ [µM] | $SI_{90}$ |
|---|---|---|---|---|---|---|---|---|---|
| Vero 76 | USA_WA1/2020 | 0.002 | VYR | — | — | — | 6.2 | >100 | >16 |
| Vero 76 | MUC-IMB-1 | 0.0002 | RT-qPCR | 10.0 | 88 | >10.0 | — | — | — |
| Vero B4 | MUC-IMB-1 | 0.0002 | RT-qPCR | 6.8 | >100 | >14.7 | — | — | — |
| CaCo-2 | MUC-IMB-1 | 0.001 | VYR | 7.5-15 | >60 | >4-8 | 15-30 | >60 | >2-4 | adult subjects with COVID-19 as determined by adverse events (AEs), serious adverse events (SAEs) and laboratory values.

To explore viral titers, measures of viral virulence and inflammatory markers during the patient's therapy, the following biomarkers are evaluated:

Virologic measures include the proportions of patients with positive virus RNA detection over time and virus RNA titer area-under-the-curve (AUC) measurements. A) SARS-CoV-2 mean viral load—log 10 copies per swab, sputum and stool, and B) Qualitative virological clearance of nasopharyngeal or respiratory samples (negative rate of SARS-CoV-2 RT PCR test for upper respiratory tract specimens, two consecutive negative tests).

Biochemistry markers as detected and monitored are D-dimer, LDH, C-reactive protein (CRP), IL-17, IFN-γ, IL-1ß, IL-6, TNFa, seroconversion, and IgM and IgG neutralizing antibodies.

For SOC, the investigator chooses among all standard of care therapies (including IV fluids, supportive therapies and medications, oxygen supplementation and others) and may, at its own discretion, choose any the following antiviral treatments (generic or branded versions, monotherapy or combination treatments, including fixed combination treatments):

Neuraminidase inhibitors (e.g., oseltamivir and its generic versions, zanamivir)
Favipiravir
Remdesivir
Ribavirin (also known as tribavirin), including its generic versions (e.g. Copegus, Rebetol, Ribasphere, Moderiba)
Interferon alfa-2b/ribavirin systemic (Rebetron)
Interferon alpha 2a or 2b, inclusive any pegylated versions
Chloroquine and hydroxychloroquine, if given in combination with azithromycin
Dolutegravir+rilpivirine (JULUCA®)
Dolutegravir+lamivudine (DOVATO®)
Ritonavir+lopinavir (KALETRA®)
Bictegravir+tenofovir alafenamide+emtricitabine (BIKTARVY®)
Dolutegravir+abacavir+lamivudine (TRIUMEQ®)
Elvitegravir+cobicistat+emtricitabine+tenofovir alafenamide (GENVOYA®)
Elvitegravir+cobicistat+emtricitabine+tenofovir disoproxil fumarate+emtricitabine (STRIBILD®)

Not accepted as antiviral treatment is Arbidol. The use of tocilizumab for patients with suspected cytokine release syndrome is allowed.

Patients are randomized 1:1 so that half of the patients receive IMU-838 plus SOC, and half receive a matching placebo plus SOC for up to 14 days. The treatment is given as double-blinded treatment and only emergency unblindings for patient's safety are allowed. After 14 days of treatment with study drug, study drug is discontinued, but all patients are free to continue with investigator's choice of standard of care treatment (including antiviral therapy, if indicated), and there are no longer any restrictions regarding concomitant medications or use of other antiviral therapies not acceptable as SOC. The patients are assessed at Day 28 for an end-of-study assessment.

IMU-838 of was tested in a Phase 2 trial with 223 patients. This trial showed preliminary evidence of clinical activity in hospitalized patients with moderate coronavirus disease 2019 (COVID-19) on following endpoints:

Time to clinical recovery: The proportion of patients reaching clinical recovery at day 7 was 18.5% (N=15) in IMU-838 treated patients, compared with only 12.8% (N=10) in the placebo arm. At day 28, 71.3% (N=57) of the IMU-838 treated patients had recovered compared with only 66.7% (N=58) in the placebo arm (full analysis set (FAS)).

Time to clinical improvement: Time to clinical improvement was found to be shorter in the IMU-838 treatment arm, as compared to placebo, and the incremental benefit increased over time (modified full analysis set (mFAS))

The proportion of patients reaching clinical improvement (as assessed by the investigators) at day 14 was 42.7% (N=38) in IMU-838 treated patients compared with only 38.5% (N=35) in the placebo arm (FAS). At day 28, the numbers were 90.9% (N=90) and 87.4% (N=90), respectively. The relative proportion of patients not improving was 6.8% greater in the placebo arm than the IMU-838 treatment arm at 14 days, and 27.7% greater at 28 days.

Following day 14, patients treated with IMU-838 experienced a numerically higher probability of clinical improvement (centrally calculated) compared with those on placebo. For instance, the 75% probability to reach clinical improvement was accelerated by 2.9 days in IMU-838 treated patients, as compared to placebo (mFAS).

The third patient quartile for duration of hospitalization (75% of patients have a shorter hospitalization duration and 25% have a longer duration of hospitalization) was shortened by 3.4 days in IMU-838 treated patients, as compared to placebo (mFAS).

Clinical improvement (centrally calculated) was observed to be better when IMU-838 was used early in the COVID-19 disease course (within the first 8 days after onset of symptoms, mFAS).

High-Risk Patients and Patients Aged Over 65 Years Experienced a More Substantial Treatment Benefit from IMU-838 than in the General Patient Population:

The 75% probability to reach clinical improvement (based on investigator assessment) was accelerated by 3.8 days in IMU-838 treated high-risk patients[6], as compared to placebo (FAS).

The 75% probability[5] to reach clinical improvement (based on investigator assessment) was accelerated by 4.8 days in IMU-838 treated elderly patients (65 years or older), as compared to placebo (FAS).

In the group of elderly patients (65 years or older), IMU-838 contributed to a faster improvement in WHO scores by at least two points, as compared to placebo (mFAS). At day 14, 36.4% (N=8/22) of the elderly patients reached a WHO score improvement by two points following treatment of IMU-838, whereas only 22.2% (N=4/18) of the elderly patients reached such improvement following placebo treatment at day 14.

Viral Burden as Well as Biochemical Inflammation and Disease Markers:

An anti-viral effect of IMU-838 on SARS-CoV-2 was observed by viral titers at the end of the treatment period (day 14) and at the end of the study (day 28).

An anti-inflammatory effect of IMU-838 was observed based on a more effective reduction of Creactive protein (CRP), a well-known marker for inflammation in the blood, in IMU-838 treated patients, as compared to placebo.

A more effective reduction of D-dimer, a well-known prognostic disease marker for COVID-19, was observed in IMU-838 treated patients, as compared to placebo.

IMU-838 was found to be safe and well-tolerated in hospitalized patients with moderate COVID-19. No general safety signals regarding new or more severe adverse events were observed for IMU-838 in this patient population, as compared to placebo. In addition, IMU-838's rate of serious adverse events and adverse events leading to treatment discontinuation was not increased, as compared to placebo. The trial also found fewer COVID-19 related adverse events with increased intensity in IMU-838 treated patients (7.1%), as compared to placebo (12.6%) and IMU-838 did not intensify any hematological effects of COVID19. In addition, IMU-838 did not increase the rate of infections and infestations as well as the rate of liver events in patients with COVID-19, as compared to placebo.

Inhibition of Overshooting Immune Response in a so-Called Cytokine Storm by Blocking Cytokine Production in Hyperactivated Immune Cells A key advantage of DHODH inhibition using IMU-838 in general, is that the sensitivity of specific immune cells to DHODH inhibition correlates with their intracellular metabolic activation state, and therefore do not negatively impact "normal" cells of the immune system but is selective for hyperactivated immune cells.

In studies, IMU-838 was able to block the T-cell mediated cytokine production of hyperactivated immune cells. In animal studies of IMU-838, animals treated with large doses of the active moiety of IMU-838 were shown to lack detrimental effects on bone marrow, supporting the lack of an unspecific anti-proliferative effect regularly seen with many traditional immunosuppressants.

In the context of COVID-19, this effect is helpful for limiting the overexuberant inflammatory response ("cytokine storm"), without shutting down the whole immune system, which is a major complication in severe cases of COVID-19.

In Vitro Antiviral Activity of IMU-838 in Combination with Remdesivir

IMU-838 was tested for in vitro antiviral activity against SARS-CoV-2 alone or in combination with remdesivir. The assay was conducted using Vero 76 cells and the test media was MEM with 2% FBS and gentamicin.

The virus was prepared in test media to achieve the lowest possible MOI that would yield >80% CPE within 5 days. Plates were infected after addition of compound as described below. The MOI for this study was 0.002.

The compound was received from the sponsor in powder form. Compound was solubilized in DMSO to prepare a 100 mM stock solution. Remdesivir was purchased from Med-Chem Express.

Compounds were tested at 10, 5, or 1 µM. Each concentration was tested alone or in combination with each concentration of the other compound. Compounds were added to wells of a 96-well plate with 80-100% confluent cells. Plates were incubated at 37±2° C., 5% $CO_2$.

For virus yield reduction assays, the supernatant fluid from each compound concentrations was collected on day 3 post infection (3 wells pooled) and virus titer was quantified using a standard endpoint dilution $CCID_{50}$ assay and titer calculations using the Reed-Muench (1948) equation after 5 days of incubation on Vero 76 cells.

Results: No toxicity was observed at any of the drug concentrations, including wells that contained both compounds. Antiviral results of combination treatment are shown in Table 5. IMU-838 reduced the titer of SARS-CoV-2 by >1 log 10 $CCID_{50}$ at the 10 µM concentration, but all other concentrations did not reduce virus titer. Remdesivir was effective in reducing virus titer by >1 log 10 $CCID_{50}$ at doses of 10 and 5 µM. Combination of IMU-838 and remdesivir appeared to have a synergistic effect at an IMU-838 concentration of 10 µM and a remdesivir concentration of 1 µM, which combination reduced virus titer to below the levels of detection (Table 5). Additionally, there appears to be a potential additive effect of IMU-838 at 1 µM with remdesivir at 5 µM (Table 5). Overall, there does appear to be a beneficial effect of combination treatment with IMU-838 with remdesivir in Vero 76 cells infected with SARS-CoV-2.

TABLE 5

Virus titer for each combination.

|  |  | Remdesivir (µM) | | | |
| --- | --- | --- | --- | --- | --- |
|  |  | 10 | 5 | 1 | 0 |
| IMU-838 | 10 | <0.67 | <0.67 | <0.67 | 4.5 |
| µM | 5 | <0.67 | 1.7 | 4.5 | 5.7 |
|  | 1 | <0.67 | <0.67 | 5.5 | 5.7 |
|  | 0 | <0.67 | 1.7 | 5.0 | 5.7 |

Virus titer units are 50% cell culture infectious doses ($CCID_{50}$)/ml

A more detailed study has since been published recently by Hahn et al. (*Viruses* 2020; 12:1394), coming to a similar conclusion.

The invention claimed is:

1. A method for treating a viral infection caused by a coronavirus in a mammalian subject comprising administering to said subject an effective amount of a DHODH inhibitor compound according to Formula (I),

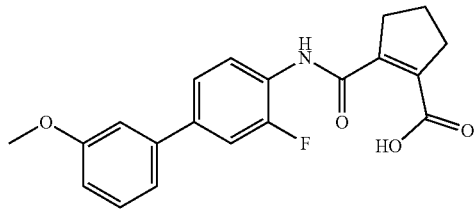

Formula (I)

a pharmaceutically acceptable salt, a solvate, a solvate of a salt, or a hydrate thereof.

2. The method according to claim 1, wherein said viral infection is caused by a betacoronavirus.

3. The method according to claim 1, wherein said compound is administered in combination with a different DHODH inhibitor, and/or in combination with a standard antiviral therapy (SAT).

4. The method according to claim 3, wherein said standard antiviral therapy (SAT) comprises administering at least remdesivir.

5. The method according to claim 3, wherein said subject is administered an effective amount of a DHODH inhibitor compound according to Formula (I) and an effective amount of said standard antiviral therapy (SAT in a DHODH inhibitor/SAT ratio of from 0.1 to 10).

6. The method according to claim 1, wherein said compound is administered to said subject in a dosage of 45 mg daily, taken as 22.5 mg BID in the morning 15-60 min before a meal, and in the evening at least 2 hours after any meal.

7. The method according to claim 1, wherein said compound is administered to said subject at between 5 to 14 days post infection.

8. The method according to claim 1, wherein said mammalian subject is a human.

9. The method according to claim 2, wherein said betacoronavirus is HCoV-OC43, SARS-CoV-1, HCoV-HKU1, MERS-CoV or SARS-CoV-2.

10. The method according to claim 9, wherein said betacoronavirus is SARS-CoV-2.

11. The method according to claim 2, wherein said betacoronavirus is a variant of SARS-CoV-2.

12. The method according to claim 1, wherein said subject is suffering from respiratory disease, acute respiratory disease, sepsis, acute respiratory distress syndrome, or an adverse immune reaction.

13. The method according to claim 1, wherein said subject is suffering from a disease caused by SARS-CoV-2.

14. The method according to claim 3, wherein said standard antiviral therapy (SAT) comprises administering at least one of:
(a) a neuraminidase inhibitor;
(b) favipiravir;
(c) remdesivir;
(d) ribavirin (tribavirin);
(e) interferon alfa-2b/ribavirin systemic;
(f) interferon alpha 2a or 2b, optionally in pegylated form;
(g) chloroquine or hydroxychloroquine (given in combination with azithromycin);
(h) dolutegravir+rilpivirine;
(i) dolutegravir+lamivudine;
(j) ritonavir+lopinavir;
(k) bictegravir+tenofovir alafenamide+emtricitabine;
(l) dolutegravir+abacavir+lamivudine;
(m) elvitegravir+cobicistat+emtricitabine+tenofovir alafenamide; or
(n) elvitegravir+cobicistat+emtricitabine+tenofovir disoproxil fumarate+emtricitabine.

15. The method according to claim 3, wherein said DHODH inhibitor/SAT ratio is from 0.2 to 10.

16. The method according to claim 3, wherein said DHODH inhibitor/SAT ratio is from 0.2 to 1.

17. The method according to claim 3, wherein said DHODH inhibitor/SAT ratio is from 1 to 10.

18. The method according to claim 1, wherein said compound is administered to said subject at between 5 to 11 days post infection.

19. The method according to claim 1, wherein said compound is administered to said subject at between 7 to 11 days post infection.

20. The method according to claim 1, wherein said compound is administered to said subject immediately post infection.

21. The method according to claim 1, wherein said compound is a dihydrate of 1-cyclopentene-1-carboxylic acid, 2-(((3fluoro-3'-methoxy(1,1'-biphenyl)-4-yl)amino) carbonyl)-, calcium salt (2:1) with the structure shown in Formula (II):

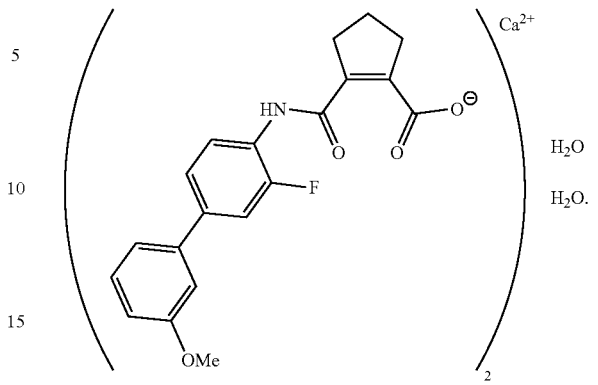

Formula (II)

22. The method according to claim 21, wherein said compound is in the form of a polymorph characterized by an X-ray powder diffraction pattern having characteristic peaks at 2 theta (±0.2°) of 5.91°, 9.64°, 16.78°, 17.81°, 19.81° and 25.41°.

23. The method according to claim 1, wherein the DHODH inhibitor is administered to the subject twice a day for at least two weeks.

24. The method according to claim 1, wherein the DHODH inhibitor is formulated for oral administration.

25. The method according to claim 1, wherein the DHODH inhibitor is administered to the subject as a tablet.

26. The method according to claim 1, wherein the viral infection causes the subject to have a cytokine storm.

27. The method according to claim 1, wherein said DHODH inhibitor compound is in the form of a calcium, potassium, choline, or sodium salt.

28. The method according to claim 1, wherein said coronavirus is a mutated form of SARS-CoV-2.

29. The method according to claim 4, wherein said DHODH inhibitor compound is a dihydrate of 1-cyclopentene-1-carboxylic acid, 2-(((3fluoro-3'-methoxy(1,1'-biphenyl)-4-yl)amino)carbonyl)-, calcium salt (2:1) with the structure shown in Formula (II):

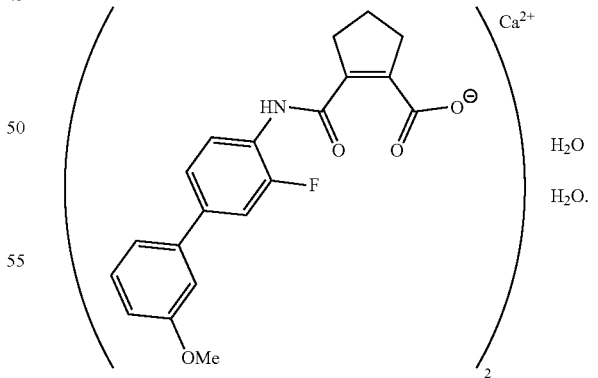

Formula (II)

* * * * *